(12) United States Patent
Bakke et al.

(10) Patent No.: US 9,045,812 B2
(45) Date of Patent: Jun. 2, 2015

(54) METHODS TO RECOVER CESIUM OR RUBIDIUM FROM SECONDARY ORE

(71) Applicant: Cabot Corporation, Boston, MA (US)

(72) Inventors: Bart Bakke, The Woodlands, TX (US); Claude Deveau, Pinawa (CA)

(73) Assignee: Cabot Corporation, Boston, MA (US)

( * ) Notice: Subject to any disclaimer, the term of this patent is extended or adjusted under 35 U.S.C. 154(b) by 0 days.

(21) Appl. No.: 14/277,914

(22) Filed: May 15, 2014

(65) Prior Publication Data

US 2014/0255278 A1     Sep. 11, 2014

Related U.S. Application Data

(63) Continuation of application No. 14/191,468, filed on Feb. 27, 2014.

(60) Provisional application No. 61/772,946, filed on Mar. 5, 2013.

(51) Int. Cl.
| | |
|---|---|
| *C22B 26/10* | (2006.01) |
| *B02C 23/08* | (2006.01) |
| *B07C 5/34* | (2006.01) |
| *C22B 1/00* | (2006.01) |
| *C22B 3/04* | (2006.01) |

(52) U.S. Cl.
CPC ............... *C22B 26/10* (2013.01); *B02C 23/08* (2013.01); *Y10T 428/2982* (2015.01); *B07C 5/34* (2013.01); *C22B 1/00* (2013.01); *C22B 3/04* (2013.01)

(58) Field of Classification Search
None
See application file for complete search history.

(56) References Cited

U.S. PATENT DOCUMENTS

| | | | |
|---|---|---|---|
| 4,542,648 A | 9/1985 | Vinegar et al. | |
| 4,597,955 A | 7/1986 | Mein | |
| 6,015,535 A | 1/2000 | Brown et al. | |
| 7,323,150 B2 | 1/2008 | Bakke et al. | |
| 2010/0219109 A1* | 9/2010 | Roos et al. | 209/3.1 |
| 2011/0288679 A1 | 11/2011 | Tavakkoli et al. | |

FOREIGN PATENT DOCUMENTS

| | | |
|---|---|---|
| WO | 2010042994 A1 | 4/2010 |
| WO | 2013006896 A1 | 1/2013 |

OTHER PUBLICATIONS

Mining and Quarry World, Sorters Reduce Mining Costs and Increase Profits, vol. 6, Issue 3, Sep. 2009.*
Namibia Rare Earths engages Mintek for metallurgical test work on Lofdal, Jul. 3, 2012.*
Pascoe et al., Efficiency of Automated Sorter Performance Based on Particle Proximity Information, Minerals Engineering 23 (2010), 806-812.*
Alden, A., "How to Identify Minerals: 10 Steps to Mineral Identification," http://geology.about.com/od/minderal_ident/ss/beginminident_2-9.htm, Sep. 26, 2011, (8 pages).
Bulled, D., "A New Full Colour Ore Sorter for Rocks Too Small to Hand Sort," Endustriyel Hammaddeler Sempozyumu, 1997, pp. 92-96.

(Continued)

*Primary Examiner* — Melissa Swain

(57) ABSTRACT

A method to recover cesium, rubidium, or both from secondary ore is described and involves using scans and sorting techniques. Refined secondary ore is further described.

30 Claims, 4 Drawing Sheets

(56) References Cited

OTHER PUBLICATIONS

Iovea et al., Dual-Energy Computer Tomography and Digital Radiography Investigation of Organic and Inorganic Materials, ECNDT 2006—Poster 44, (13 pages).
Pascoe et al., "Efficiency of automated sorter performance based on particle proximity information," Minerals Engineering, vol. 23, 2010, pp. 806-812.
Redwave, ""Redwave" Mineral Sorting Systems," Mineral sorting REDWAVE for mining industry, (no date on brochure), (13 pages).
Selway et al., "The Tanco Pegmatite at Bernic Lake, Manitoba. XIV. Internal Tourmaline," The Canadian Mineralogist, vol. 38, 2000, pp. 877-891.
Siddiqui et al., "Dual-Energy CT-Scanning Applications in Rock Characterization," Society of Petroleum Engineers, SPE Annual Technical Conference and Exhibition, Houston, Texas, SPE 90520, Sep. 2004, pp. 1-9.
Von Ketelhodt et al., "Dual energy X-ray transmission sorting of coal," The Journal of the Southern African Institute of Mining and Metallurgy, vol. 110, Jul. 2010, pp. 371-378.
International Search Report and Written Opinion issued in corresponding International Patent Application No. PCT/US2014/019295, dated Aug. 11, 2014 (15 pages).
Butterman et al., "Mineral Commodity Profiles Cesium," XP009179337, http://pubs.usgs.gov/of/2004/143212004-1432.pdf, Jan. 1, 2005, (13 pages).
Butterman et al., "Mineral Commodity Profiles Rubidium," XP-002727772, http://pubs.usgs.gov/of/2003/of03-045/of03-045.pdf, Jul. 22, 2003, pp. 1-11.
Manouchehri, H.R., "Sorting: Possibilities, Limitations and Future," Proceedings of Mineral Processing Conference, XP002727721, Feb. 1, 2003, pp. 1-17.
Von Ketelhodt, Lutke, "TOMRA Sorting Solutions SAIMM—Johannesburg," XP002727773, http:/www.saimm.co.za/download/branches/Johannesburg/SAIMM%20%20%20Regional%20Meeting%20-%20sensor%20Based%20sorting%20LvK%2020120517.pdf, May 17, 2012, (38 pages).

\* cited by examiner

US 9,045,812 B2

METHODS TO RECOVER CESIUM OR RUBIDIUM FROM SECONDARY ORE

This application is a continuation of U.S. patent application Ser. No. 14/191,468, filed Feb. 27, 2014, which claims the benefit under 35 U.S.C. §119(e) of prior U.S. Provisional Patent Application No. 61/772,946, filed Mar. 5, 2013, which is incorporated in its entirety by reference herein.

BACKGROUND OF THE INVENTION

The present invention relates to cesium or rubidium or both and the recovery of these elements from secondary ore. The present invention further relates to a purified ore that contains cesium and a unique combination of others minerals and/or elements.

Cesium salts, such as cesium formate, are increasingly being discovered as useful components or additives for a variety of industrial applications, such as in the hydrocarbon recovery areas. However, deposits of "primary" ore, that is, ore that contains high amounts of cesium with insignificant amounts of undesirable impurities, are rare, and operators have long sought techniques to enhance recovery of cesium and/or rubidium from known deposits of secondary ore containing cesium and/or rubidium.

However, cesium-containing secondary ore, while available, presents major problems with regard to recovering the cesium from such ore. For instance, the expense of recovering significant amounts of cesium from low yield ore can be quite time consuming and expensive based on known methods. Also, with known techniques, it is very difficult and expensive to separate cesium from certain undesirable metals or minerals that can typically be found with deposits of cesium-containing secondary ore. For instance, many cesium-containing secondary ore deposits have significant lithium containing minerals, such as, but not limited to, phosphate minerals, such as Amblygonite, Montebrasite, and/or cesium-substituted Lithiophosphates. If the phosphate minerals which contain significant amounts of lithium, and frequently sodium, are not significantly separated from the secondary ore, the lithium can then present serious impediments to the commercial use of the cesium-containing fraction of the secondary ore in a variety of industries, such as in the hydrocarbon recovery area with regard to fluids, such as drilling fluids, completion fluids, packer fluids, and the like.

In more detail, one beneficial use of cesium is as cesium formate in solution to create high density well fluids which are extremely useful in deep drilling oil and gas wells. If the lithium is present at excessive levels in the fluids, the fluid cannot be manufactured with a sufficient amount of cesium in solution to achieve the high fluid density required for well drilling fluids. If the lithium levels exceed critical parameters, the cesium-containing salt will precipitate out of solution before reaching the needed density to work as a suitable well fluid, which will make the fluid unsuitable for hydrocarbon recovery.

In using primary ore sources, the presence of lithium is not a significant problem because the cesium-containing primary ore deposits, namely, pollucite, can be recovered without any significant levels of lithium-containing phosphate minerals being present. Thus, this problem is unique to cesium-containing secondary ores. In addition, if the lithium is not substantially removed from the secondary ore before chemical processing to recover cesium, the lithium, as well as any sodium, can be excessively challenging to remove from the cesium during traditional downstream wet chemical processing of the ore (e.g., beginning with acid digestion). Adding to this challenge is the variable presence of the levels of these lighter alkalis, as introduced with the ore prior to wet chemical processing.

These same problems also can exist with rubidium containing ore or ore containing cesium and rubidium.

Accordingly, there is a need in the industry to develop methods for recovering the highly sought and valued minerals bearing cesium, rubidium, or both, from secondary ore, also referred to as cesium-containing secondary ore. There is a further need to create methods that will significantly reduce the content of minerals bearing lithium, and the other lighter alkali, impurities and other mineral and/or metal impurities in the recovered cesium, rubidium, or both, so as to avoid the significant challenges of wet chemical processing, as well, the viability of brine products, as per those problems described above.

SUMMARY OF THE PRESENT INVENTION

A feature of the present invention is to provide a method to effectively recover cesium, rubidium, or both, from secondary ore.

A further feature of the present invention is to provide methods to utilize the cesium, rubidium, or both, recovered from secondary ore in the production of cesium-containing fluids, such as cesium formate and the like.

An additional feature of the present invention is to provide a method to recover cesium, rubidium, or both, from secondary ore and yet control the amount of lithium and/or metals or minerals that would be otherwise present in the recovered ore.

A further feature of the present invention is to provide a crushed cesium-containing purified ore that contains high amounts of cesium and controlled amounts of lithium or lithium ions and having desirable cesium oxide-to-phosphorus oxide weight ratios.

Additional features and advantages of the present invention will be set forth in part in the description that follows, and in part will be apparent from the description, or may be learned by practice of the present invention. The features and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method to recover cesium, rubidium, or both from secondary ore. The secondary ore can contain 25 wt % $Cs_2O$ or less based on overall weight of the secondary ore (such as 15 wt % or less or 10 wt % or less) and the majority of the secondary ore can include pieces having at least one dimension that is over 5 inches. The method can include crushing the secondary ore to obtain crushed ore comprising individual pieces. Each individual piece has a size capable of passing through a mesh/screen or bar/screen of 3 inches. Or, one can start with the crushed ore from a source or supplier. The method includes passing the crushed ore through a first sorter to conduct a first sorting at a feed rate of at least 1 ton/hour, wherein the first sorter determines whether each individual piece of crushed ore is a "Grade 1 piece" or "Grade 2 piece," based on the first sorter conducting at least one scan of each individual piece and determining or calculating atomic number and/or material density of each individual piece, wherein said "Grade 1 piece" is determined or calculated to comprise $Cs_2O$ in an amount of at least 20 wt % based on the weight of said individual piece. The method involves separating the Grade 1 pieces from the Grade 2 pieces, wherein % $Cs_2O$ of the total amount of Grade 1 pieces is at least 10% by weight higher than the total wt % $Cs_2O$ in the secondary ore. The method can optionally include extracting cesium, rubidium or both by subjecting the Grade 1 pieces to at least one acid treatment and/or other chemical treatment. It is recognized that the pollucite mineral, in nature, can have differing $Cs_2O$ wt % content due to the varying degree of lighter alkali molar substitution for $Cs_2O$. Pollucite comprising 44 wt % $Cs_2O$ would be about the maximum found in this mineral. For purposes of the present invention, a level of about 32 wt % $Cs_2O$ can be considered to represent "pure" pollucite mineral, and generally the pollucite mineral can contain no more than 32 wt % to 44 wt % $Cs_2O$.

The present invention further relates to a crushed cesium-containing purified ore. For instance, the crushed cesium-containing purified ore can have the following:
 a) optionally, a pollucite and/or nanpingite and/or carnallite content in an amount of from 10 wt % to 90 wt %;
 b) a $Cs_2O$ content of from 5 wt % to about 32 wt %;
 c) total phosphate mineral content of from 1 wt % to 10 wt %;
 d) a % $P_2O_5$ content of about less than 1.5% wt %;
 e) a % $Cs_2O$: % $P_2O_5$ weight ratio of at least 4:1;
 f) a $Li_2O$ content of from 0.5 wt % to 2 wt %; and
 g) an average crushed ore size or thickness of from 0.1 inch to 5 inches such as 0.5 to 2.5 inches, wherein all wt % are based on weight of purified ore. For this purified ore, a) the pollucite content is optional and further, instead of pollucite, any cesium bearing mineral(s) can be substituted in part or entirely, such as nanpingite and/or carnallite.

The crushed cesium containing purified ore can additionally have one or more of the following:
 a) a SQUI content in an amount of from 0.5 wt % to 5 wt %;
 b) a quartz content in an amount of from 0.5 wt % to 5 wt %;
 c) a total Feldspar content of from 1 wt % to 10 wt %;
 d) an Albite content of from 0 wt % to 1 wt %;
 e) an Amphibolite content of from 0.1 wt % to 0.5 wt %;
 f) an Apatite content of from 0.5 wt % to 4 wt %;
 g) a Lepidolite content of from 2 wt % to 8 wt %; and/or
 h) an Amblygonite content of from 0 wt % to 1 wt %.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the features of the present invention and together with the description, serve to explain the principles of the present invention. The descriptions are not intended to limit the scope or the spirit of the invention.

DETAILED DESCRIPTION OF THE PRESENT INVENTION

Figure 1:
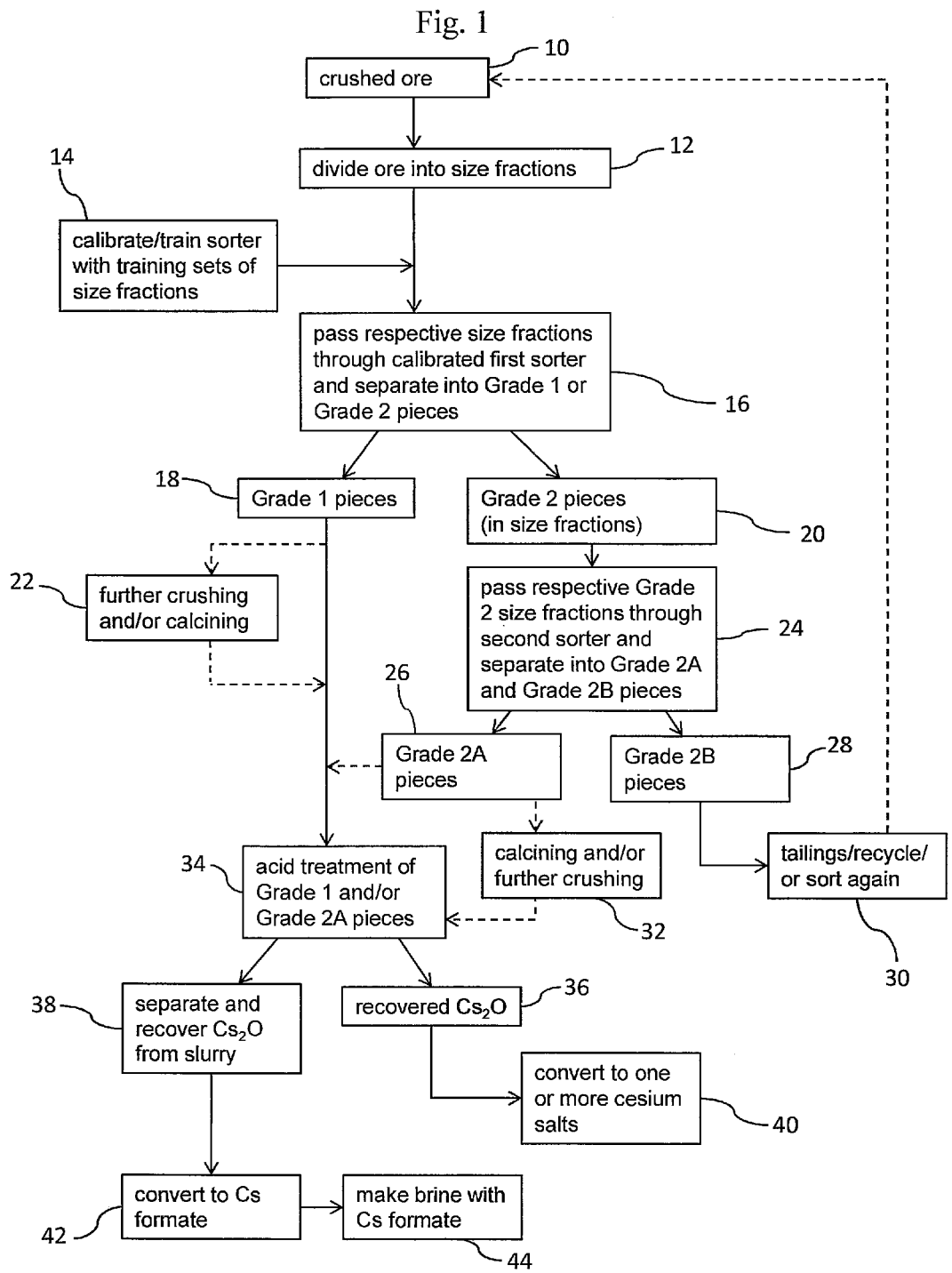
FIG. 1 is a flow diagram showing one process of the present invention for recovering cesium, rubidium, or both, from secondary ore.

According to the present invention, a method to recover cesium, rubidium, or both, from secondary ore (also known as cesium-containing secondary ore) is described. The present invention further relates to the recovered highly purified cesium-containing ore (also known as crushed cesium-containing purified ore). The present invention further relates to fluids or other material that contains the recovered cesium in the form of elemental cesium or a cesium compound (e.g., salt). Instead of cesium, the recovery and use of rubidium or a mixture of cesium and rubidium can be achieved. Further, the processes of the present invention can also be used to recover potassium from secondary ore. Also, to be clear, while less useful, the processes of the present invention can be used with primary ore alone, secondary ore alone, or a combination of primary and secondary ores. FIG. 1 provides a flow chart of steps that can be used. In all instances, the crushed cesium-containing purified ore contains an insufficient quantity of lithium-containing phosphate minerals to interfere with industrial uses of cesium, rubidium, cesium compound, or rubidium compound obtained by further refinement of the crushed cesium-containing purified ore.

In more detail, in the present invention, methods to recover cesium, rubidium, or both from secondary ore are provided. The secondary ore can comprise 25 wt % $Cs_2O$ or less based on overall weight of the secondary ore. The majority (by weight) of the secondary ore can comprise, consists essentially of, or consist of pieces having at least one dimension that is over 5 inches. Thus, over 50 wt % of the secondary ore has at least one dimension or two dimensions or all dimensions over 5 inches, such as over 60 wt %, over 70 wt %, over 80 wt %, over 90 wt %, over 95 wt %, over 99 wt % or about 100 wt %, based on the total weight of the starting secondary ore. Put another way, prior to crushing, a majority of the ore (by wt %) does not fall through a 5 inch U.S. mesh/screen.

The secondary ore (overall) can be or include 20 wt % $Cs_2O$ or less, 15 wt % $Cs_2O$ or less, 10 wt % $Cs_2O$ or less, from 1 wt % to 15 wt % $Cs_2O$, from 1 wt % to 10 wt % $Cs_2O$, from 0.25 wt % to 5 wt % $Cs_2O$, less than 1 wt % $Cs_2O$, about 0.1 wt % $Cs_2O$ or more, from 0.1 wt % to 20 wt % $Cs_2O$, from 0.1 wt % to 18 wt % $Cs_2O$, from 0.1 wt % to 15 wt % $Cs_2O$, from 0.1 wt % to 10 wt % $Cs_2O$, from 0.1 wt % to 5 wt % $Cs_2O$, from 1 wt % to 20 wt % $Cs_2O$, from 1 wt % to 18 wt % $Cs_2O$, from 1 wt % to 15 wt % $Cs_2O$, or other low amounts of cesium containing ore, or other amounts within or outside of any one of these ranges based on the total wt % of the starting secondary ore.

The secondary ore can include, comprise, consist essentially of, or consist of pollucite, nanpingite, carnallite, rhodozite, pezzottaite, rubicline, borate ramanite, beryls, voloshonite, cesstibtantite, avogadrite, margaritasite, kupletskite, nalivkinite, petalite, spodumene, lepidolite, biotite, mica, muscovite, feldspar, microcline, Li-muscovite, lithiophilite, amblygonite, illite, cookeite, albite, analcime, squi, amphiboles, lithian mica, amphibolite, lithiophospahe, apatite and/or londonite, or any combinations thereof. The secondary ore can comprise, consist essentially of, or consist of pollucite, an aluminosilicate mineral having the general formula $(Cs>Na)[AlSi_2O_6]H_2O$. The secondary ore can have at least 1 wt % pollucite based on the weight of the secondary ore, or from 1 to 5 wt % pollucite based on the weight of the secondary ore, or at least 3 wt % pollucite based on the weight of the secondary ore. Other amounts are from 1 wt % to 20 wt % or from 1 wt % to 15 wt %, or from 1 wt % to 10 wt %, or from 1 wt % to 5 wt % pollucite based on the weight of the secondary ore.

In FIG. 1, a flow chart is provided to provide steps that can be used in the methods of the present invention. It is noted that this is simply exemplary of the present invention and is not intended to limit the steps or sequence of steps or which steps can be used or which steps can be optional. In FIG. 1, the ore can be crushed or crushed ore can be received (10) and then the crushed ore can be divided into various size fractions (12). At some point in time, the sorter that is used can be calibrated or trained with training sets of size fractions (14) based on the size fractions obtained in (12). It is noted that step (14) can be practiced at any point prior to running size fractions through the sorter and for instance, can be done minutes before passing size fractions through the sorter or hours or days or months beforehand. Then, the size fractions from the crushed ore are passed through the sorter that is calibrated and separated into Grade 1 or Grade 2 pieces (16). The Grade 1 pieces (18) are the pieces that contain high amounts of cesium oxide or have the potential to contain cesium oxide. The Grade 1 pieces (18) can then optionally be further crushed and/or calcined (22). The Grade 1 pieces can be optionally merged with the Grade 2A pieces (26). The Grade 1 pieces (18) can optionally be subjected to acid treatment with or without the Grade 2A pieces (34). The acid treatment (34) permits the separation of the cesium-containing product from the other materials (38). Conventional separation techniques known in the art can be used. Then, the recovered cesium can optionally be converted to cesium formate (42). The cesium formate can then be made into a brine that contains cesium formate for a variety of uses (44). As a further option, after acid treatment (34) of the Grade 1 pieces, the recovered cesium product, such as $Cs_2O$ (36) can then be used to form one or more types of various cesium salts, such as cesium hydroxide, cesium sulphate, and the like (40). The Grade 2 pieces that are separated in step (16) can be recovered as Grade 2 pieces (20). These Grade 2 pieces can be optionally passed through a second sorter, which can be the same as the first sorter (24). This step separates the Grade 2 pieces into Grade 2A and Grade 2B pieces. The Grade 2A pieces (26) can optionally be merged with the Grade 1 pieces as described above, or the Grade 2A pieces can be calcined or further crushed (32) and then optionally subjected to acid treatment (34) for further processing. The Grade 2B pieces (28) can be considered tailings or can be recycled and passed through the sorter again for further recovery of desirable products (30).

The method can comprise, consists essentially of, or consist of crushing the secondary ore to obtain crushed ore that is or includes individual pieces. Or in the alternative, crushed secondary ore can be obtained. Each individual piece can have a size capable of passing through a U.S. mesh/screen or bar/screen of 3 inches (e.g., or a U.S. mesh size of 2.5 inches, or 2 inches, or 1 inch, or smaller mesh size). The method further includes passing the crushed ore through a first sorter to conduct a first sorting at a feed rate of at least 1 ton/hour. The first sorter determines whether each individual piece of crushed ore is a "Grade 1 piece" or "Grade 2 piece", based on the first sorter conducting at least one scan of each individual piece and determining or calculating atomic number and/or material density of each individual piece. For purposes of the present invention, "the estimated atomic number" or "determining or calculating atomic number" can be atomic number or effective atomic number, also known as $Z_{eff}$, which is the atomic number of a compound or material. For "material density", this can be considered "mass density". To avoid any doubt, when "atomic number" or "estimated atomic number" is used throughout, this can be or include "effective atomic number" for instance using Mayneord's method. The "Grade 1 piece" is determined or calculated (based on the scan) to have $Cs_2O$ in an amount of at least 5 wt % (e.g., at least 5 wt %, at least 10 wt %, at least 15 wt %, at least 30 wt % from 5 wt % to 32 wt % or more) based on the weight of the individual piece. The method further includes separating the Grade 1 pieces from the Grade 2 pieces, wherein total wt % $Cs_2O$ of the total (combined) Grade 1 pieces is at least 10% by weight higher (e.g., at least 20 wt % higher, at least 30 wt % higher, at least 40 wt % higher, at least 50 wt % higher, at least 75 wt % higher, at least 100 wt % higher, at least 250 wt % higher, at least 400 wt % higher, at least 600 wt % higher, at least 800 wt % higher, at least 1000 wt % higher) than the total wt % $Cs_2O$ in the secondary ore before sorting.

As another option, the Grade 1 pieces can be determined or calculated e.g., based on a scan, to comprise $Cs_2O$ in an amount and concentration, each by weight, of at least twice that present in the starting ore or secondary ore, and/or in an amount and concentration, each by weight, of at least twice that present in the Grade 2 pieces that are recovered (or separated from the Grade 1 pieces).

With regard to the secondary ore as the starting material, the secondary ore can have at least one dimension, or at least two dimensions, or three dimensions that are over 5 inches in size. For instance, the starting secondary ore, prior to being crushed, can be 5.1 inches in at least one dimension, such as from 5.1 inches to 100 inches or more, such as from 10 inches to 75 inches, from 6 inches to 50 inches, and the like. Essentially, the secondary ore can be any size over 5 inches since it will be subjected to crushing to reduce the size as indicated herein prior to sorting.

With regard to the crusher, any crusher can be used that can reduce large rocks into smaller rocks or individual pieces that can be scanned as described herein. Examples of crushers that can be used include, but are not limited to, a jaw crusher, a gyratory crusher, a cone crusher, an impact crusher, such as a horizontal shaft impactor, hammer mill, or vertical shaft impactor. Other examples of crushers that can be used include compound crushers and mineral sizers. As an option, a rock breaker can be used before crushing to reduce oversized material too large for a crusher. Also, more than one crusher can be used and/or more than one type of crusher can be used in order to obtain desirable sizes and processing speeds.

In the crushing step, prior to the first sort, the secondary ore can be crushed to obtain crushed ore that is or includes individual pieces, where each individual piece has a size capable of passing through a mesh/screen of 3 inches, or passing through a mesh/screen of 1 inch, or passing through a mesh/screen of 0.5 inch, or passing through a mesh/screen of 0.25 inch, or passing through a mesh/screen of 0.1 inch (all U.S. mesh sizes).

The feed rate to the first sorter (and/or through the first sorter) can be at least 1 ton/hour or at least 2 ton/hour, at least 5 ton/hour, at least 8 ton/hour, at least 10 ton/hour, at least 15 ton/hour, at least 20 ton/hour, at least 25 ton/hour, at least 30 ton/hour, from 1 ton/hour to 35 ton/hour, from 5 ton/hour to 35 ton/hour, and the like.

With regard to feeding the crushed ore to the first sorter, any means to convey this material can be used, such as a belt, chute, vibrating table, or other conveying devices used to move rocks or gravel to a location on a production line or mining operation.

For purposes of the present invention, 'determining' atomic number and/or density can include 'calculating' or even estimating atomic number and/or density. With regard to the first sorter, the sorter is capable of performing at least one scan and, preferably, at least two scans of each individual piece and thereby calculating or determining an atomic number and/or material density of each individual piece or portions thereof. This calculating or determining based on one or more scans can be considered an estimate of atomic number and/or material density. The calculating or determining of the atomic density can be considered an estimated atomic density. The calculating or determining of the material density can be considered an estimated material density. If more than one scan, the scans can be done simultaneously, almost simultaneously, or sequentially. The sorter can, by the scan, determine the estimated atomic number and/or material density of each individual piece or portions thereof, and this scan information, such as by X-ray scanning, can be used to determine which piece should be accepted or ejected. The scan information can be converted to optical images or pictures of each individual piece (or a portion(s) thereof) for subsequent use in the scanning operations. The optical images, as further explained elsewhere, can be color coded a) based on estimated atomic number and/or material density of the overall individual piece; b) based on the overall average estimated atomic number and/or average material density of the individual piece (where the average can be determined based on volume of each atomic number region and/or material density region measured), or c) based on where pixels or regions of an image of the individual pieces can be assigned different colors per estimated atomic number and/or material density of that pixel or region. Thus, an individual piece can have different zones that reflect different atomic numbers and/or material densities due to different minerals/elements present in the same individual piece. Based on the scan and the estimated atomic number and/or material density, different colors can be used to denote acceptable material or unacceptable material. Put another way, color codes can be associated with each individual piece or portions of each individual piece to signify individual pieces that contain $Cs_2O$ in sufficient amounts or pieces that do not contain sufficient amounts of $Cs_2O$, or contain an excessive amount of unacceptable material such as phosphates or lithium oxide.

The sorter can be a dual energy X-ray transmission (DEXRT) sorter. For instance, a Commodas Ultrasort sorter can be used for the sorting. To obtain a more accurate sort as described herein, the sorter can be optionally "trained" or calibrated to understand which types of minerals or rocks or fractions thereof would be considered as having the desired $Cs_2O$ amount and, thus, be a Grade 1 piece. Similarly, rock types can be used to train the sorter on which types of rock types or portions thereof would not be desirable and, therefore, would not contain high amounts of $Cs_2O$ and, therefore, be considered a "Grade 2 piece." When the sorter is being trained, generally, representative rocks or fractions thereof that are found in the location of the mining where the secondary ore is mined or otherwise recovered are used for training. Thus, in this optional "training" session, one would go to the mining location and collect representative rocks that reflect accurately the types of rocks or fractions thereof that are found. These rocks or fractions thereof are then identified by the user with respect to what type of rock that they are and/or whether the rock is a cesium containing rock which generally contains the mineral pollucite (and/or nanpingite and/or carnallite). The training session calibrates the sorter to better distinguish "Grade 1 pieces" from other rocks. The training can greatly increase the accuracy of identifying Grade 1 and Grade 2 pieces. When rocks of known composition are passed through the sorter for training or calibration, the scan can be studied to identify scan properties suitable for selection of Grade 1 pieces or pollucite containing pieces. While one option in the present application is to set the sorter to screen for a desired atomic number and/or material density, another option is to simply set the sorter's scan parameters to match the readings obtained from each training set. Put another way, if through the training sets, the sorter obtains a reading "X" for estimated atomic number and/or "Y" for a material density for a representative Grade 1 piece for a particular size fraction, then when the training is done, the sorter can be programmed to identify pieces that have this "X" atomic number and/or "Y" density number, or have an atomic number and/or material density that is within 5%, within 10%, within 15%, within 20%, or within 25% or some other designated percentage within the "X" and/or "Y" readings from each size fraction in each training set. This would be done for each size fraction used in the training set.

In training the sorter, various training sets can be used. For example, various identified or known minerals can be used, such as three to eight (or more) different mineral types, can be used to train. Each training set can comprise the same mineral types but have a different size fraction. The purpose of using different size fractions is to accurately calibrate the sorter to handle various sizes of rocks, or fractions thereof, when detection and sorting are based in part on overall averages determined for a volume of regions measured. For instance, one or more of the following five size fractions (U.S. Standard Sieve Size) can be used to calibrate or train the sorter:

−2 inches+1.5 inches
−1.5 inches+1 inch
−1 inch+0.5 inch
−0.5 inch+0.25 inch
−0.25 inch+0.125 inch.

The rock types that can be included in each training set can be: Pollucite, Lepidolite, one or more pieces of Feldspar, Quartz, SQUI, Amblygonite, and/or Albite and/or one or more other mineral/rock types. Out of these rock types, the Grade 1 pieces are the pollucite mineral and the rest of the materials are, for the most part, Grade 2 pieces. Again, the rock types that are used during the training session are representative or are actual rocks obtained from the mining location so as to accurately reflect the rocks or fractions thereof that will be passed through the sorter during production of sorted ore. The training sets can contain Grade 1 pieces and/or Grade 2 pieces. The training set may contain desirable pieces (e.g., cesium containing pieces) and undesirable pieces (e.g., non-cesium containing pieces or where the cesium amount is very low).

The following are further explanations of the type of rock types and one example of a training set used for purposes of "training" the sorter as described herein. The training set can comprise the following eight mineral types in different rock size fractions and/or grain sizes.

1. Pollucite is by far the most important cesium containing mineral in this test. In the ore sample used for this test, the overall cesium was approximately 10 wt % $Cs_2O$. With visual mineral identification and manual separation, a pollucite training sample was created comprising approximately 30 wt % $Cs_2O$. This sample can contain 70-80 wt % of the $Cs_2O$ to be recovered, depending on size fraction.

2. Lepidolite is an important source of rubidium. Lepidolite mineral typically contains in excess of s 2.3 wt % $Rb_2O$. Lepidolite can be a critical mineral in the training set for rubidium.

3. Feldspar having a $Ta_2O_5$ (identified as Feldspar 4).

4. Feldspar having $Rb_2O$ (identified as Feldspar 3).

5. Quartz can make up 15-20 wt % of the ore by weight and has no commercial value.

6. SQUI (Spodumene Quartz Intergrowth) can be an important mineral for spodumene production (to recover $Li_2O$). Spodumene is the mineral class which contains the most cesium other than the pollucite. The cumulative distribution of $Cs_2O$ for the pollucite and SQUI including all other mineral classes was 97% in the −2"+1.5" size fraction. $Cs_2O$ grade in the spodumene went from the +8% in the −2"+1.5" fraction to +4% in the −1"+0.5" fraction.

7. Amblygonite (and/or Montebrasite) can be a major source of $P_2O_5$ in the ore. Amblygonite is a nuisance mineral.

8. Albite which generally does not contain cesium oxide or rubidium oxide.

Below is a further description of some of the minerals that can be found in secondary ore. One or more of these can be used in the "training" sets as described herein.

| Rock/Mineral | Description |
| --- | --- |
| SQUI | Clearish White; medium to coarse grained; prominent Spodumene and Quartz intergrowths |
| Quartz | Clear to White; minor rose color; massive |
| Smoky Quartz | Clear grey to Smoky Grey; coarse grained crystals to massive |
| Aplitic Albite | Bluish Grey; fine grained; massive; forms bands in contact with smoky quartz and feldspar crystals |
| Spodumene | Greenish White; well developed cleavage; lath shaped crystals |
| Siliceous (Pervasive) | Greyish White; very fine grained; sugary texture; Quartz & Feldspar also present |
| Rusty Feldspar/ Quartz | Rusty staining or very fine grained reddish clear crystals; host rock is medium to coarse grained pink to grey Feldspar & smoky quartz; minor fine grained tourmaline |
| Grey Feldspar/ Quartz | Medium grained; equigranular; minor spodumene and tourmaline |
| Amblygonite | Opaque White; massive; soapy feel; cleavage faces; minor grey quartz and feldspar |
| Green Yellow Patches | Weathered mica or staining; host rock is fine to coarse grained Feldspar & Quartz; Vuggy spots; minor spodumene and siliceous pieces |
| Lepidolite | Purplish grey; fine to medium grained; grey K-feldspar with purple lepidolite seams and blebs |
| White Feldspar | Whitish; medium to coarse grained; uniform; white K-feldspar with clear quartz; minor smoky quartz |
| Grey Feldspar | Greyish; coarse grained; slightly mottled; good cleavage; yellowish mica seams; minor white quartz |
| Pink Feldspar & Wallrock | Pinkish black; medium grained; varies from grey feldpsar with mottled grey quartz to anhedral pinkish feldspar and black amphibolite wallrock; scattered schorl tourmaline crystals |
| Grey Feldspar & Wallrock | Greyish black; coarse grained; grey K-feldspar and smoky quartz; wallrock inclusions; tourmaline; minor lepidolite |
| Feldspar with black microseams | Greyish; K-feldspar and quartz; Narrow black micaeous seams in Feldspar |
| Large Mica | 1-5% medium to coarse grained mica; mica clear to silvery in color; surface curvilinear; host rock either medium grained grey Feldspar & quartz or fine grained reddish perthite |
| Siliceous Matrix | Clearish grey; Clear quartz and grey K-feldpsar in very fine grained matrix |

Using the above size fractions, the crushed ore comprising individual pieces, for example, are separated into five (5) size fractions, namely, (a) −2 inches+1.5 inches; (b) −1.5 inches+1 inch; (c) −1 inch+0.5 inch; (d) −0.5 inch+0.25 inch; and (3) −0.25 inch+0.125 inch. For purposes of the present invention, other size fractions of various size spreads also can be used to calibrate or train the sorter. Once the training is done for the sorter using various size fractions, it is to be understood that no further training is needed and the sorter is now calibrated. The sorter simply needs to be set to the desired size fraction that will then be passed through the sorter(s).

When using the calibration or training sets or running the actual secondary ore through the sorter, the rocks or fractions thereof should only have a one layer thickness. In other words, the rocks or fractions thereof should not be on top of each other and this is so that a scan of each individual rock can occur and so that the scan can identify which rock is a Grade 1 piece or a Grade 2 piece.

As an option, size fractions of the crushed ore that are below 0.125 inch or less than 3 mm are not sorted through the sorter. In addition, as an option, size fractions above 3 inches, or above 2.5 inches, or above 2 inches are not passed through the sorter. The sizes above 3 inches or 2 inches can optionally be passed through the crushing step again to further reduce the size, such as below 2.5 inches or to below 2 inches.

As an option, multiple size fractions can be used to train the sorter or calibrate the sorter and then be used to separate the crushed ore into these respective size fractions for passing through the sorter. The following formulas can be used to determine the various size fractions:

$$S_1 = S_x \text{ to } 50\% S_x$$

$$S_2 = S_1 \text{ to } 50\% S_1$$

$$S_3 = S_2 \text{ to } 50\% S_2$$

$$S_4 = S_3 \text{ to } 50\% S_3$$

and so on, following this formula to create additional size fractions, if desired, where x is the maximum size fraction that can pass through the sorter, such as 3 inches, 2.75 inches, 2.25 inches, or 2 inches, or other sizes. Instead of $S_1$ to $S_4$, one can use more size fractions or less size fractions, like $S_1$-$S_3$, or $S_1$-$S_5$, or $S_1$-$S_6$.

As an option, the size fraction below 0.125 inch or below 3 mm can optionally not be passed through the sorter, and this small size fraction of crushed ore can simply be mixed with the "Grade 1 pieces" as an option. Through various experiments, it was determined that this small size fraction does not negatively affect quality of the "Grade 1 pieces" that are obtained and does not affect the desirable $Cs_2O$ amount. This was considered quite unexpected and surprising and permits a beneficial use for this very small size fraction.

Using the training sets, the sorter can be better programmed (for instance by using the images of the training sets to know what is Grade 1 pieces and what are Grade 2 pieces) so as to better separate the Grade 1 pieces from the Grade 2 pieces. The sorter can be programmed using (at least in part) the images of the training sets to separate rubidium-bearing rocks, non-cesium containing rocks, low grade cesium-bearing rocks, and amphiboles from the Pollucite-containing Grade 1 pieces.

The scan performed in the methods of the present invention can be a computer tomography type such as a dual energy computer tomography scan. The dual energy scan and the method involved can involve reconstructing the distribution function of the linear attenuation coefficient (LAC) within a chosen section, which can be planar (surface area) or volumetric. With the high energy scanner, LAC projections can be acquired, for instance, by measuring the current density of the transmitted energy ray for consecutive positions along a direction perpendicular to the incident radiation. The LAC distribution can be reconstructed from the scanned areas (the individual pieces) by means of a filtered back projection method, iterative least square technique or algebraic reconstruction (see for instance, Kak et al (1999) Principles of Computerized Tomographic Imaging, IEEE Press, New York; Natterer (1986) The Mathematics of Computerized Tomography, J. Wiley & Sons, New York; Brooks et al (1976) Principles of computed assisted tomography CAT in radiography and radioisotopic imaging. Physics in Medicine and Biology 21, 689-752; and Censor et al (2001) Component averaging: an efficient iterative parallel algorithm for large and sparse unstructured problems, Parallel Computing 27, 777-808, all incorporated in their entirety by reference herein). The energy ray can be X-ray or a gamma-ray. For the dual energy scans, the lower energy scan (or low channel) should be at least 10 kV (or 10 keV) different from the higher energy scan (or high channel). Preferably, the lower energy scan is below 100 kV and the higher energy scan is above 100 kV. For instance, the lower energy scan can be 40 to 90 kV and the higher energy scan can be 120 to 200 kV. The image acquisition and processing can be automated with programming and software, such as, but not limited to, Accent Pro 2000 software such as Tomo software including the Data Acquisition Program and Tomogram Reconstruction Program; or Avizo Analysis Software for image acquisition and processing, all commercially available.

For purposes of the present invention, the scans can determine the LAC of the individual pieces and this can represent the product between density ρ and the mass attenuation coefficient (MAC). The formula that can be used is described in Rizescu et al. (2001) Determination of local density (or material density) and effective atomic number by the dual-energy computerized tomography method with the 1921r radioisotope, Nuclear Instruments and Methods in Physics Research A. 465, 584-599, incorporated in its entirety by reference herein. With this determination, the photoelectric effect and Compton's inelastic scattering can be taken into account. With the dual energy scan in the present invention, a determination of both material density and effective atomic numbers distribution functions through the individual pieces can be made.

With X-rays, the transmitted radiations can be detected by means of sets of two different detectors separated by a metal shield, such as a thin (1 to 2 mm) copper shield. The metallic foil can act as a filter for the low energy X-rays, which modifies the spectral composition of the radiation detected by each set of detectors. This dual energy detection in optional combination with the training sets (calibration sets) having known densities and atomic numbers, and by using suitable reconstruction algorithms, two different CAT or digital images of the individual pieces can be computed where one image can represent the material density and the other image can depict the $Z_{eff}$ distribution over the investigated pieces. As an option, the two different digital images, where one represents material density and the other depicts estimated atomic number or a $Z_{eff}$ distribution, can be merged or overlapped into a single image to reflect both computations. This combination of the two images, one for material density and one for atomic number, can be useful in determining or deciding whether an individual piece of crushed ore is a "Grade 1 piece" or "Grade 2 piece." This merging or combination of two images into one image can also be referred as an "effective atomic density." For purposes of sorting, and as an option, this "effective atomic density" can be used to determine if an individual piece of crushed ore is a "Grade 1 piece" or "Grade 2 piece" based on the percent of the individual piece that satisfies both the desired atomic number and desired material density that is used, for instance, based on the training or calibration sets for that particular size fraction.

Various types of devices can be used to pass the individual pieces through the scanners, namely, the pieces can be directed to and pass through the scanner using a free-fall method without any rotating components or a belt can be used to achieve feeding of the individual pieces through the scanner. The sorter can have a feeder to form a monolayer of individual pieces that pass the scanner, and this can be achieved with a vibratory feeder. A feed belt can then be used to feed the individual pieces between the X-ray source and the sensor. As stated, instead of a feed belt, a chute can be used without a belt. As the individual pieces pass between the source and sensor, preferably a dual energy X-ray, an image(s) of each rock (individual piece) is acquired and analyzed by an image processor.

Then, a separation chamber can be used. The separation chamber is where the individual pieces proceed after being scanned and, based on the scan and image analysis, the individual pieces follow a separation plate onto a conveyor or bin. In the separation chamber, the Grade 1 pieces are separated from the Grade 2 pieces, and this can be done by using air jets to blast out the piece from the normal trajectory. The separation chamber can be set up either to blast out the Grade 1 pieces, which would then be considered ejected pieces, and the Grade 2 pieces can maintain their normal or natural trajectory and, therefore, be considered "accepted." The opposite can be set up as well, wherein the Grade 2 pieces are blasted out as ejected, and the Grade 1 pieces are left as accepted. Either setup is possible, depending upon user preferences.

A broad-band electrical X-ray source(s) can be applied to the individual pieces to be sorted. The X-ray sensor system for instance, produces a digital image of the material being sorted, preferably using two different energy bands. The X-ray attenuation through the material is different in the two bands and depends on both the material's thickness and material density. An image transformation of the density images of the two bands can be done so as to classify each pixel according to atomic number and/or material density. In lieu of each pixel, a group of pixels or other region/zone can be classified collectively. A classification of the ore pieces (also known as individual pieces for this invention) is then made with regard to $Cs_2O$ content. As stated in more detail herein, the first sorter can be set such that the Grade 1 piece is determined based on having an estimated atomic number, for instance, of at least 50 for a certain percentage volume of the individual piece (e.g., over 20%, over 30%, over 40%, over 50%, over 60%, over 70%). In other words, if the individual piece scanned is determined to contain a certain percentage of volume or surface area with an estimated atomic number of at least 50, this would be considered a Grade 1 piece that will be separated from the Grade 2 pieces. As an alternative or in addition, the individual piece can have the material density of the individual piece or portion thereof determined or calculated. For instance, if the scan determines that the individual piece or a significant volume of the individual piece, such as over 20% or over 30% or over 40% or over 50% or over 60% by volume, has a material density of at least 2.7 g/cm³ or at least 2.75 or at least 2.8 or at least 2.85 or at least 2.9, or has a density from 2.7 to 3.2 or a density from 2.7 to 3.2 or a density of 2.8 to 3.1 or a density of 2.7 to 3 or 2.8 to 3.1, the individual piece can be separated and considered a Grade 1 piece. Ideally, with two scans, the estimated atomic number and the material density can be both considered as criteria for determining if the piece is a Grade 1 piece or not. In other words, as an option, in order for a Grade 1 piece to be separated from Grade 2 pieces, the Grade 1 piece must have the desired estimated atomic number and the desired material density as described above and herein. Or, as an option, an individual piece can be considered a Grade 1 piece if one of two criteria are satisfied; meaning, the individual piece has either the desired estimated atomic number or the desired material density or both. Needless to say, if both criteria are required, the accuracy of recovering Grade 1 pieces increases significantly. Density (or material density) can be considered in units of g/cm$^3$.

The sensor's high spatial resolution can be 0.8 mm or 1.6 mm or other resolutions above or below these numbers or in between. The resolution permits the evaluation of particle shape, particle size, material thickness and texture of a grey-scale image (inclusions of various densities). The X-ray transmission image processing provides a highly efficient sensor system for classifying materials. The sorter can work with an electric X-ray source featuring a maximum acceleration voltage of 160 KV and other acceleration voltages can be used.

Figure 2:
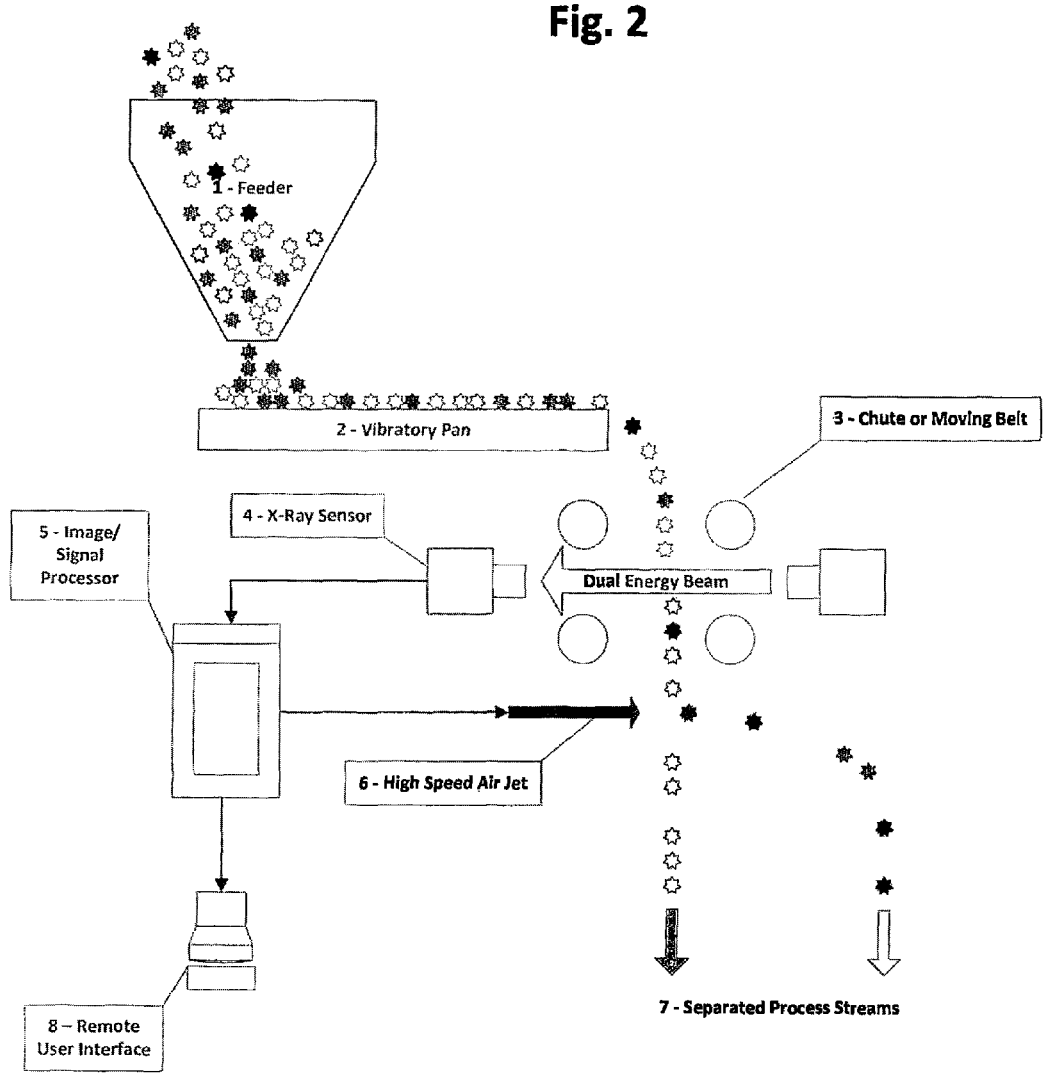
FIG. 2 is a diagram showing the general set-up of the sorter that can be used in the methods of the present invention.
Figure 3:
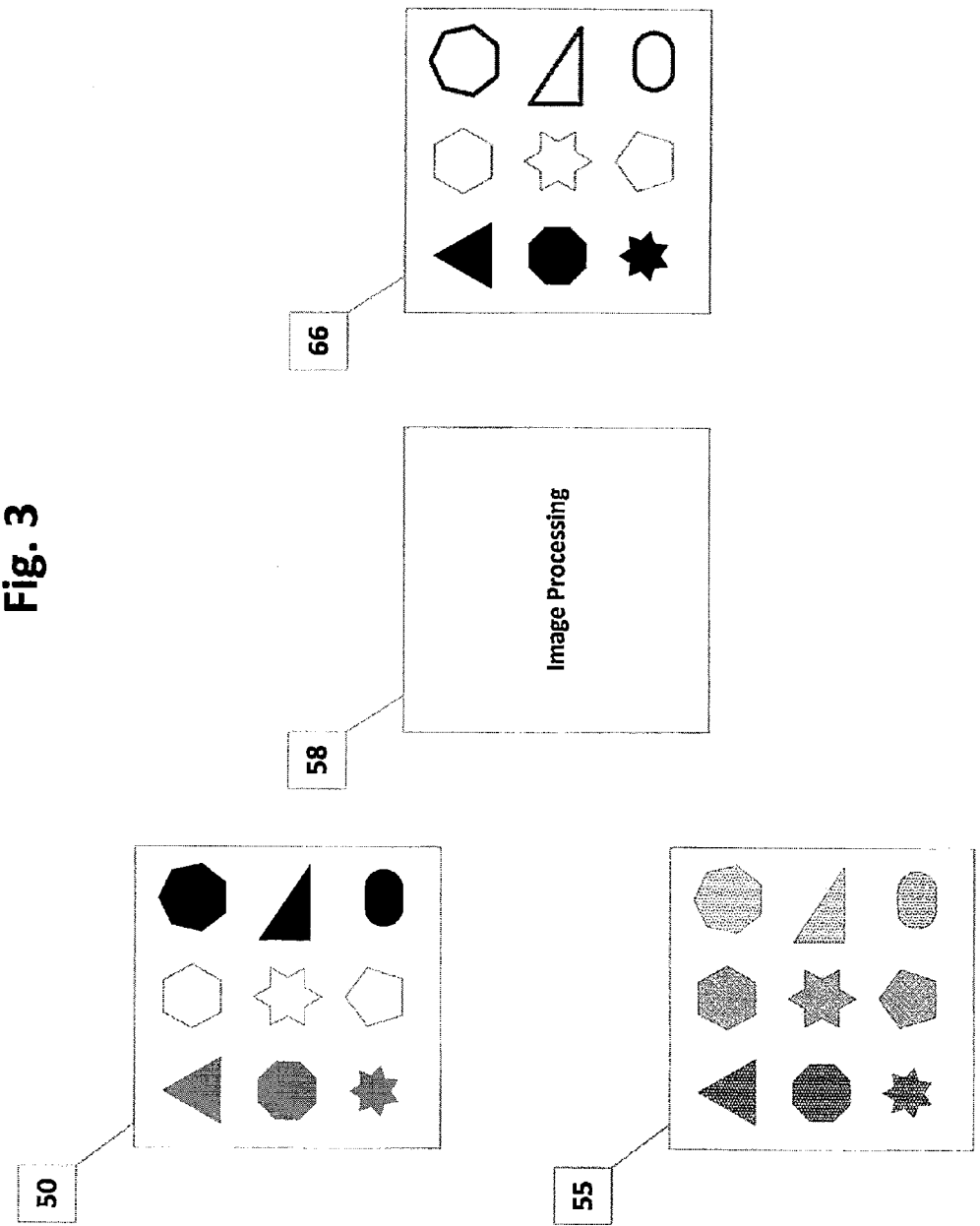
FIG. 3 is a diagram showing a representation of a scan using a high channel and low channel signal scan with signal to image processing to create an image of the rocks to activate or achieve a mechanical separation of rock grades.

FIG. 3 provides one example of where the sorter does an X-ray scan (as shown in FIG. 2) using two different energies, and as shown in FIG. 3, a low channel image (50) can be created and a high channel image (55) can be created and then these two images can be subjected to image processing (58) to determine atomic number and material density per pixel or pixels or other desired volume or surface area. Further, the image processing can create images (66) of each piece and assign particular colors to particular ranges of atomic numbers and densities detected or determined or calculated and, as an option, the sorter can determine ejects and accepts based on the assigned atomic number and/or material density alone or it can determine ejects and accepts once the image is converted to a color image and color sorting can be used based on the digital image to sort, which is using an optical sorter method. For instance, a pixel or pixels or other volume having an effective atomic number above 50, for instance, from 50 to 80, can be assigned a black color. Different sub-ranges of effective atomic number within 50 to 80 can be assigned different colors, such as black (for one sub-range), blue (for a second sub-range), or green (for a third sub-range), depending upon where the effective atomic number lies with regard to this range of from 50 to 80. Effective atomic numbers that are below 50, for instance, can be assigned a color red or other color(s) and, therefore, the sorter, if one chooses, can be operated based on this color assignment as an optical sorting based on the image created, which reflects the estimated atomic number of the rock or portion thereof. In addition or alternatively, the color designation can be used with material density using the same approach, and as described above, where a density of at least 2.7, or other ranges described earlier are used.

The sorter, through the image processing, can further determine if the majority (by volume, for instance) of the individual piece primarily has an atomic number and/or material density that would characterize it as a Grade 1 piece or a Grade 2 piece. For instance, if the individual piece contains at least 10% by volume, at least 20% by volume, at least 30% by volume or at least 40% by volume or at least 50% by volume (or surface area) of a desired atomic number (e.g. 50 to 80) and/or material density (e.g. 2.7 to 3.2 g/cm$^3$), then the piece can be considered a Grade 1 piece. This determination can be adjusted based on user preferences.

In the methods of the present invention, the first sorter can be set such that the Grade 1 piece is determined based on a determined or calculated atomic number of at least 50, or based on a determined or calculated atomic number of at least 52, or based on a determined or calculated atomic number of at least 53, or based on a determined or calculated atomic number of from 50 to 80 or from 50 to 70, or from 50 to 60, or from 51 to 60, or from 52 to 60, or from 53 to 60 for a certain percent volume of the individual piece, such as at least a 10% volume, at least a 20% volume, at least a 30% volume, or at least a 40% volume, or at least a 50% volume, or at least a 60% volume, or at least a 70% volume, or at least a 80% volume, or at least a 90% volume. The % volume can be determined based on the number of pixels having the desired atomic number. The % volume can be determined based on computed tomographic (CT) scans or slices. Or, the first order can be set such that the Grade 1 piece is determined based on a determined or calculated material density of at least 2.7, or based on a determined or calculated material density of at least 2.75, or based on a determined or calculated material density of at least 2.8, or based on a determined or calculated material density of at least 2.9, or based on a determined or calculated material density of from 2.7 to 3.2 or from 2.8 to 3.1 or 2.85 to 3.2 or 2.9 to 3 for a certain percent volume of the individual piece, such as at least a 10% volume, or at least a 20% volume, or at least a 30% volume, or at least a 40% volume, or at least a 50% volume, or at least a 60% volume, or at least a 70% volume, or at least an 80% volume, or at least a 90% volume. The % volume can be determined based on the number of pixels having the desired atomic number. The % volume can be determined based on CT slices. As stated, in the methods of the present invention, the first sorter can be such that the Grade 1 piece is determined based on both the atomic number and material density as described herein using the various ranges described herein.

As shown in FIG. 2, which is simply a schematic diagram of the operation in simplified format, the crushed ore enters a material feed 1 and this crushed ore then is fed to a vibratory pan 2, which spreads the particles into a monolayer, wherein the monolayer of crushed ore in the form of individual pieces can be fed by chute 3 or by a moving belt (not shown) and passes through a dual energy beam X-ray sensor 4 (or other energy scan). Cameras can be used or other sensors can be used including, but not limited to, X-ray transmission, X-ray fluorescence, X-ray fluorescence spectroscopy, conductivity, near infra-red spectroscopy sensors, and the like. Upon passing through the scanners, a high speed image/signal processor 5 can process the scanned information to determine atomic number and/or material density of each individual piece and to then determine whether the piece is a Grade 1 piece or a Grade 2 piece. As stated, the determination of atomic number and/or material density can be done on a per pixel basis and then a determination can be made on whether a sufficient percent by volume of each individual piece has the desired atomic number and/or material density. As stated, this information can optionally be processed into the form of an image of the individual pieces and an array of high speed air jets can separate the individual pieces as Grade 1 pieces or Grade 2 pieces based on this processed information. The array of high speed air jet 6 can be used or other means to separate can be used. The separated process streams 7, namely the stream of Grade 1 pieces and the stream of Grade 2 pieces can then be fed to proper areas for further processing. For instance, the Grade 2 pieces can be designated as tailings and not be further used. Or, the Grade 2 pieces can be re-introduced into the sorter again under the same sorting conditions or different sorting conditions. Or, the Grade 2 pieces can be processed through a different sorter. A remote user interface 8 can be in communication with the image/signal processor for purposes of controlling the overall sorter and for making any adjustments with regard to sort classifications and calibrations.

A Grade 1 piece (for instance, from the first sort) can contain, based on the scan, at least about 4 wt %, at least about 6 wt %, at least about 8 wt %, at least 10 wt %, at least 15 wt %, at least 20 wt %, at least 25 wt %, at least 30 wt %, or from 4 wt % to 32 wt %, from 6 wt % to 30 wt %, from 8 wt % to 25 wt %, from 10 wt % to 20 wt %, from 15 wt % to 20 wt % $Cs_2O$ based on the weight of the individual piece.

The method can optionally include calcining the Grade 1 pieces after separating, and generally before any optional acid treatment or other chemical treatment. The calcining can be at a calcining temperature of from about 800° C. to about 1200° C., or other temperatures, for any amount of time, such as 10 minutes to 10 hours.

In the methods of the present invention, at least about 40% by weight of available $Cs_2O$ present in the secondary ore can be captured or recovered, such as at least about 50%, at least about 60 wt %, at least about 70 wt %, at least about 80 wt %, at least about 90 wt %, such as from 40 wt % to 95 wt %, by weight of available $Cs_2O$ that was originally present in the secondary ore.

In the methods of the present invention, as an option, at least about 10% by weight of available $Rb_2O$ present in the starting secondary ore can be captured or recovered, such as at least about 15% by weight of available $Rb_2O$ present in the secondary ore.

The methods of the present invention can optionally include a second sorting. The second sorting can comprise, consists essentially of, or consists of passing the Grade 2 pieces through a second sorter, which can be the same or different from the first sorter. The settings for the second sort can be the same or different from the first sorting. The second sorter can determine whether each individual piece of the Grade 2 pieces is a "Grade 2A piece" or "Grade 2B piece," based on the second sorter conducting at least one scan of each individual piece and determining or calculating atomic number and/or material density of each individual piece (e.g., based on per pixel and determining % volume of each atomic number and/or material density in the individual piece in a manner similar to the first sorting operation). In the second sort, the "Grade 2A piece" can be determined or calculated to comprise $Cs_2O$ and/or can be determined or calculated to comprise $Rb_2O$ in an amount of at least about 4% based on the weight of the individual piece (e.g., at least 5 wt %, at least 10 wt %, or at least 15 wt % or at least 20 wt %). As with the first sort, the second sorting includes separating the second sort Grade 2A pieces from the second sort Grade 2B pieces using the same set-up as described above and summarized in FIG. 2. The second sort Grade 2A pieces can be combined with the Grade 1 pieces from the first sort or can be processed separately.

The second sorter can be set such that the Grade 2A piece is determined based on a determined or calculated atomic number of at least 25, or based on a determined or calculated atomic number of at least 30, or based on a determined or calculated atomic number of at least 35, or based on a determined or calculated estimated atomic number of from 25 to 45, for a certain percent volume of the individual piece, such as at least a 30% volume, or at least a 40% volume, or at least a 50% volume, or at least a 60% volume, or at least a 70% volume, or at least a 80% volume, or at least a 90% volume. The % volume can be determined based on the number of pixels having the desired atomic number. The % volume can be determined based on CT slices. It has been discovered that by having the second sort use different sorting conditions with regard to atomic number, additional $Cs_2O$ can be recovered with minimal impurities. The second sort can additionally or alternatively include a scan for material density as in the first sorting using the same settings or different settings, such as reducing the minimum material density, for instance by 10% to 30% or some other amount. Equally useful, a significant level of rubidium in the form of $Rb_2O$ can be recovered using this second sorting technique, wherein the rejects of the first sorting are used and sorted through this second sorting. As an option, additional sorts can be used for the rejects of the second sort. Any number of additional sorts having the same or different conditions from the first sort or second sort can be used. The second sorting can capture at least about 1% by weight of available $Cs_2O$ present in the secondary ore, based on weight of the starting secondary ore, or at least about 15% by weight of available $Cs_2O$ present in the secondary ore, based on weight of the starting secondary ore, or at least about 50% by weight of available $Cs_2O$ present in the secondary ore, based on weight of the starting secondary ore.

With regard to the second sorting, as an option, the Grade 2A pieces can be determined or calculated to comprise $Rb_2O$ in an amount and concentration, each by weight, of at least twice that present in the Grade 2 pieces, or in an amount and concentration, each by weight, of at least twice that present in the Grade 2B pieces.

With regard to the second sorting, the second sorting can capture at least about 30% by weight of the available $Cs_2O$ present in the Grade 2 pieces, based on the weight of the Grade 2 pieces from the first sort. As an option, the second sorting can capture/recover at least 50% or at least about 70% by weight of the available $Cs_2O$ present in the Grade 2 pieces, based on the weight of the Grade 2 pieces from the first sort.

As an option, the second sorting can capture at least about 30% by weight, at least 50% by weight, at least 65% by weight of the available $Rb_2O$ present in the starting ore, namely the secondary ore, based on the weight of the starting ore at the beginning of the process.

As an option, the second sorting can capture at least about 35% by weight, at least about 50% by weight, at least about 65% by weight, or at least about 80% by weight of the available $Rb_2O$ present in the Grade 2 pieces, based on the weight of the Grade 2 pieces from the first sort.

As an option, the second sorting can capture at least about 20% by weight of available $Rb_2O$ present in the secondary ore, based on weight of the secondary ore prior to the first sorting, or at least about 30% by weight of available $Rb_2O$ present in the starting secondary ore, based on weight of the secondary ore prior to the first sorting, or at least about 40% by weight of available $Rb_2O$ present in the secondary ore, based on weight of the secondary ore at the start, or at least about 50% by weight of available $Rb_2O$ present in the secondary ore, based on weight of the starting secondary ore, or at least about 1% by weight of available $Cs_2O$ present in the secondary ore, based on weight of the starting secondary ore, or at least 5% by weight of available $Cs_2O$ present in the starting secondary ore, based on weight of the secondary ore, or at least 10% by weight of available $Cs_2O$ present in the secondary ore, based on weight of the starting secondary ore.

The first sorting and optional second sorting combined can capture at least 40% by weight of available $Rb_2O$ present in the secondary ore, based on weight of the starting secondary ore, or at least 50% by weight of available $Rb_2O$ present in the secondary ore, based on weight of the starting secondary ore, or at least 60% by weight of available $Rb_2O$ present in the secondary ore, based on weight of the starting secondary ore, or at least 65% by weight of available $Rb_2O$ present in the secondary ore, based on weight of the starting secondary ore.

The first sorting and optional second sorting combined can capture at least 60% by weight of available $Cs_2O$ present in the secondary ore, based on weight of the starting secondary ore, and/or at least 40% by weight of available $Rb_2O$ present in the secondary ore, based on weight of the starting secondary ore, or at least 70% by weight of available $Cs_2O$ present in the secondary ore, based on weight of the starting secondary ore, and/or at least 50% by weight of available $Rb_2O$ present in the secondary ore, based on weight of the starting secondary ore, or at least 80% by weight of available $Cs_2O$ present in the secondary ore, based on weight of the starting secondary ore, and/or at least 60% by weight of available $Rb_2O$ present in the secondary ore, based on weight of the starting secondary ore.

With the methods of the present invention, the Grade 1 pieces can have or include at least 100% more $Cs_2O$ based on a comparison of total weight percent of $Cs_2O$ in the secondary ore to total weight percent of $Cs_2O$ in the Grade 1 pieces, such as at least 150% more $Cs_2O$, at least 200% more $Cs_2O$, or at least 300% more $Cs_2O$ (such as 100% to 1000% more by wt) based on a comparison of total weight percent of $Cs_2O$ in secondary ore to total weight percent of $Cs_2O$ in Grade 1 pieces.

The method can optionally include extracting cesium, rubidium or both by subjecting the Grade 1 pieces to at least one acid treatment or acid digestion. The acid treatment can involve mixing the Grade 1 pieces with sulfuric acid, such as concentrated sulfuric acid, or other acids. Examples of acids that can be used include, but are not limited to, strong acid as that term is understood in the art. The acid(s) can be sulfuric acid, hydrochloric acid, hydrofluoric acid, nitric acid, and the like.

In the present invention, the Grade 1 pieces can be subjected to an acid treatment which can involve leaching the Grade 1 pieces, which typically comprise pollucite and/or nanpingite and/or carnallite, with strong sulfuric acid to obtain an extract containing cesium alum which can be recovered by crystallization. Cesium alum is cesium aluminum sulfate hydrate. The sulfuric acid extracts can typically be contaminated with other metal ions, such as rubidium, sodium, potassium, magnesium, and iron. The processes described in U.S. Pat. No. 6,436,879, can be used as part of the acid treatment to obtain a more highly pure cesium-containing material for such end uses as drilling fluids. This process, in summary, involves treating the cesium starting material with a suitable reagent to dissolve at least a portion and preferably all or nearly all of the cesium contained therein and form a slurry. A base comprising slaked lime or calcium carbonate and an acid containing the anion of the pre-determined cesium compound can be added to the slurry and then the pre-determined cesium compound, once formed, can be separated.

The Grade 1 pieces, alone or combined with the Grade 2A pieces, can be subjected to an acid treatment, such as sulfuric acid or other acids that would be considered equivalent. The acid:cesium weight ratio can be 4:1 or greater. The sulfuric acid treatment strength can be, for instance, at least 35% $H_2SO_4$, by weight. Other acids may be used at the same or similar acid strength. The acid treatment may be carried out at temperatures of 90° C. or higher. The acid treatment can continue for 15 minutes or more, e.g., for 15 minutes to 2 hours or more.

As an option, and at any part of the process, the Grade 1 and/or Grade 2A pieces can be subjected to further comminution (one or more) to achieve any nominal sizing including sizes of less than 100 microns.

In the present invention, the method can further include extracting cesium, rubidium or both by subjecting the Grade 2A pieces to at least one non-acid treatment. The non-acid treatment can involve calcining the pieces, for instance at a temperature of from about 800° C. to about 1200° C., or other temperatures, for any amount of time, such as 10 minutes to 10 hours or more.

As an option, the Grade 1 pieces which now contain a much higher percentage of $Cs_2O$ can then be processed for a variety of uses. For instance, the Grade 1 pieces can be used to form cesium compounds, such as cesium formate. For instance, the $Cs_2O$ can be recovered and subjected to further recovery processes by reacting the Grade 1 pieces with at least one salt, where the salt is capable of recovering at least one metallic element, such as cesium, to form a reaction product that includes at least one metallic element. For instance, the salt can be a sulfate salt. Details of this further processing step can be found in U.S. Pat. No. 7,323,150, incorporated in its entirety by reference herein. By using this process, the cesium can be converted to a precursor salt, such as cesium sulfate, from which other cesium salts are produced. Other methodology similarly can produce alternative cesium salts from precursors like cesium hydroxide and cesium carbonate. As described, for instance, in U.S. Pat. No. 7,759,273, the cesium can be formed into a cesium formate which subsequently can then be converted to a different cesium metal salt. Another process to form cesium salts is described in U.S. Pat. No. 6,652,820, which is incorporated in its entirety by reference herein. This method involves forming a cesium salt by reacting cesium sulfate with lime to form cesium hydroxide which can then be converted to a cesium salt, such as cesium formate. As stated, the cesium compounds can be very desirable as drilling fluids or other fluids used for hydrocarbon recovery, such as completion fluids, packer fluids, and the like.

The processes described in U.S. Pat. No. 6,015,535 can also be used to form desirable cesium compounds, such as cesium formate. The various formulations and compositions described in the following patents can be used with the cesium or cesium compounds recovered by the processes of the present invention and each of these patents are incorporated in their entirety by reference herein: U.S. Pat. Nos. 7,407,008; 7,273,832; 7,211,550; 7,056,868; 6,818,595; 6,656,989; and 6,423,802.

Figure 4:
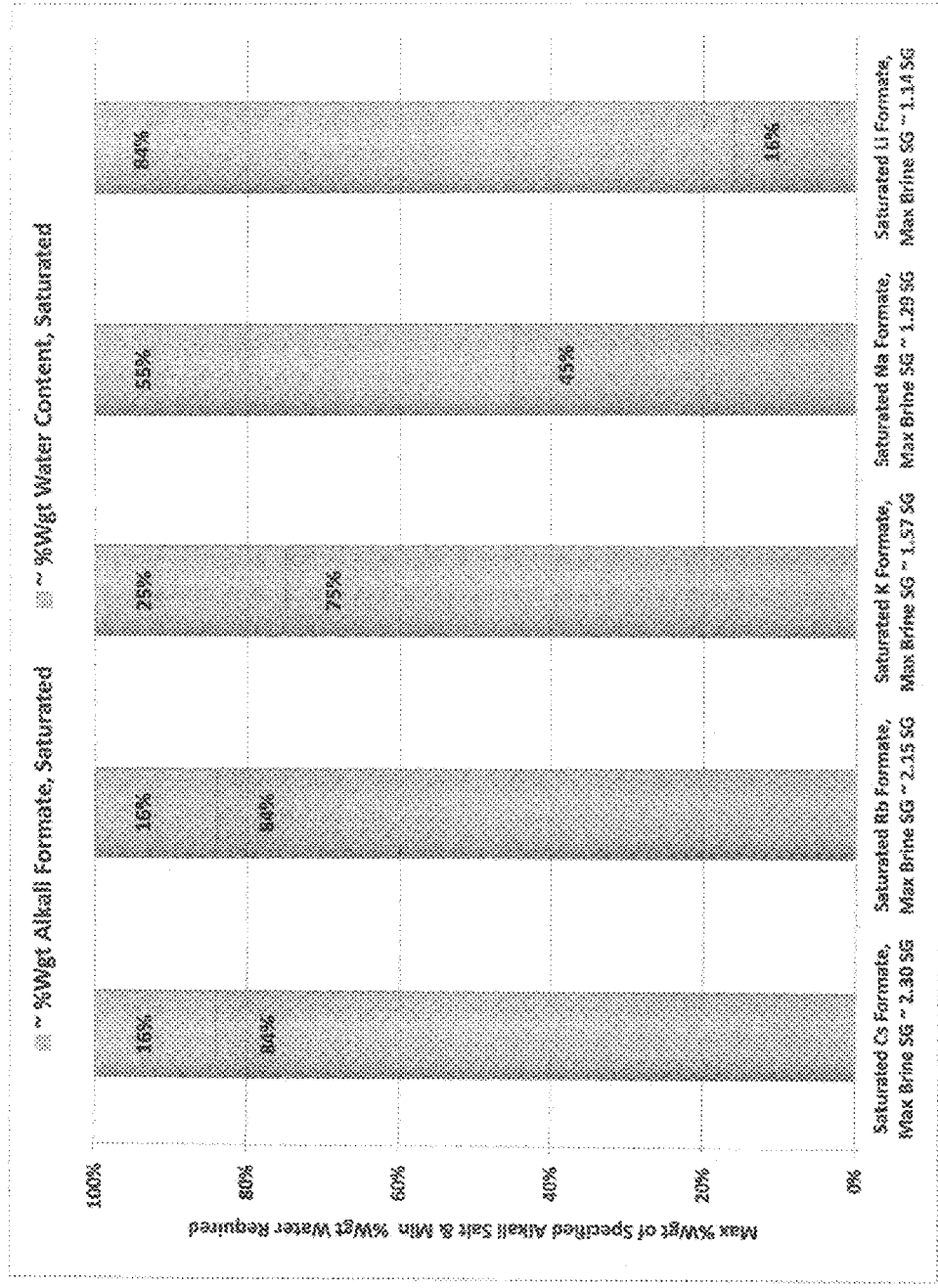
FIG. 4 is a graph shows the effects of lithium with regard to the solubility of cesium in an aqueous fluid.

As stated above and as shown in FIG. 4, a fluid comprising lithium, for instance a fluid comprising lithium formate, has a much lower saturation point than a fluid comprising cesium formate or rubidium formate. As shown in FIG. 4, cesium formate will remain in saturated solution until a maximum of 84% by weight cesium formate is present in only 16 wt % water. The same is true for a saturated rubidium formate solution. Also shown in FIG. 4 is that these blends form a very desirable, high specific gravity solution, with a specific gravity ranging from 2.15 to 2.3 SG. However, a lithium formate solution is fully saturated at 16% by weight lithium formate, and any amounts above this will cause the lithium formate salt to precipitate from solution. Further, with lithium formate fluid, the maximum brine SG (specific gravity) is only about 1.14 SG, which generally is not useful for drilling fluids where high density fluids are desired. The presence of lithium formate in a cesium formate or rubidium formate fluid tends to destabilize the fluid, causing the maximum wt % of cesium formate or rubidium formate in solution at saturation to drop significantly. Thus, the presence of lithium in the higher specific gravity cesium formate brines is highly deleterious when attempting to produce stable oil field brines. Other, less stable, lighter alkalis of sodium and potassium, as illustrated in FIG. 4, also have a negative effect on the stability of high specific gravity alkali formate brine, but are not as deleterious as lithium. If the lithium content exceeds, for instance, over 3,000 ppm with regard to the refined, crushed ore processed into drilling fluids, this can result in an inadequate or suboptimal cesium or rubidium formate drilling fluid or other high specific gravity, dense fluid. The acid treatment of cesium-containing ore to refine the ore and prepare cesium salts, such as cesium formate, cannot remove the lighter alkalis, including lithium, from the ore. This is a significant obstacle to refinement and use of secondary ore sources of cesium oxide for the manufacture of pure cesium or rubidium compounds, and high specific gravity fluids containing cesium or rubidium. As a result, the processes of the present invention are effective to significantly reduce the lithium levels in secondary ore in order to achieve a useful cesium-containing refined crushed ore intermediate product which can then be used to make high density drilling fluids or purified cesium compounds for other end uses. Prior ore refinement processes, such as flotation, acid treatment, color sorting, and the like, have not been effective to extract cesium and rubidium bearing minerals from cesium-containing secondary ore containing lithium bearing phosphate minerals, without also extracting deleterious quantities of lithium. In contrast, the atomic number and/or material density sorting method of the present invention is effective in separating cesium and rubidium bearing minerals from cesium-containing secondary ore containing lithium bearing phosphate minerals, and from phosphate minerals containing deleterious quantities of lithium.

As an option, the Grade 2 or Grade 2B pieces which contain high levels of lithium, potassium, and/or sodium can be further processed to recover the alkali metals for other industrial uses, such as batteries and other electrical applications.

The present invention further relates to novel, purified, secondary ore which contains desirable levels of $Cs_2O$ and/or $Rb_2O$. The resulting sorted ore, after the first sort, is unique by itself or in combination with the sorted ore resulting from the second sort or further optional subsequent sorts, such as a third sort, and so on.

The present invention further relates to a crushed, refined, cesium-containing ore. For instance, the crushed, refined, cesium-containing ore can have the following (where wt % are based on total weight of ore):
  a) an optional pollucite content in an amount of from about 10 wt % to about 90 wt % (e.g., from 20 wt % to 75 wt %, 30 wt % to 75 wt %, 30 wt % to 70 wt %, 35 wt % to 65 wt %, 40 wt % to 60 wt %, 45 wt % to 55 wt %; 25 wt % to 40 wt %, 50 wt % to 90 wt %, 50 wt % to 80 wt %, and the like). The pollucite content is optional for purposes of describing crushed, refined ore. Further, in lieu of or in combination with pollucite, nanpingite and/or carnallite can be present in these amounts;
  b) a $Cs_2O$ content in an amount of at least 5 wt % (e.g., at least 5 wt %, at least 10 wt %, at least 15 wt %, at least 30 wt % from 5 wt % to 32 wt %, from 10 wt % to 25 wt %, from 15 wt % to 25 wt % or more);
  c) total phosphate mineral content of from 2 wt % to 10 wt % (e.g., from 3 wt % to 8 wt %, from 4 wt % to 10 wt %, 5 wt % to 10 wt %, 6 wt % to 10 wt %, and the like);
  d) a % $P_2O_5$ content of less than about 1.5 wt %;
  e) a % $Cs_2O$: % $P_2O_5$ weight ratio of at least 4:1 (e.g., at least 5:1, at least 6:1, at least 10:1, at least 15:1, at least 20:1, at least 25:1, at least 30:1, at least 35:1, at least 40:1, at least 50:1, at least 60:1, at least 70:1, from 4:1 to 75:1, and the like);
  f) a $Li_2O$ content of from 0.5 wt % to 1.2 wt % (e.g., 0.6 wt % to 1.1 wt %, 0.7 wt % to 1.2 wt %, 0.8 wt % to 1.2 wt %, 0.9 wt % to 1.2 wt %, and the like);
  g) a $Rb_2O$ content of from 0.5 wt % to 1.8 wt % (e.g. from 0.7 wt % to 1.8 wt %, 1 wt % to 1.8 wt %, 1.3 wt % to 1.8 wt %); and
  h) an average crushed ore size of from about 0.1 inch to about 3.5 inches (e.g., 0.1 inch to 2.5 inches, 0.25 inch to 3 inches, 0.5 inch to 3 inches, 0.75 inch to 2.5 inches, 1 inch to 2.5 inches), wherein all wt % are based on weight of purified ore.

The crushed, refined, cesium containing ore can additionally have one or more of the following (based on the total weight of the ore):
  a) a SQUI content in an amount of from 0.5 wt % to 5 wt % (e.g., from 0.6 wt % to 5 wt %, from 0.7 wt % to 5 wt %, from 1 wt % to 5 wt %, from 1.2 wt % to 5 wt %, from 2 wt % to 5 wt %);
  b) a quartz content in an amount of from 0.5 wt % to 5 wt % (e.g., from 0.6 wt % to 5 wt %, from 0.7 wt % to 5 wt %, from 1 wt % to 5 wt %, from 1.2 wt % to 5 wt %, from 2 wt % to 5 wt %);
  c) a total Feldspar content of from 1 wt % to 10 wt % (e.g., from 2 wt % to 10 wt %, from 3 wt % to 10 wt %, from 4 wt % to 10 wt %, from 5 wt % to 10 wt %);
  d) an Albite content of from 0 wt % to 1 wt % (e.g., from 0.1 wt % to 1 wt %, from 0.2 wt % to 1 wt %, from 0.3 wt % to 1 wt %, from 0.4 wt % to 1 wt %);
  e) an Amphibolite content of from 0.1 wt % to 0.5 wt % (e.g., from 0.2 wt % to 0.5 wt %, from 0.3 wt % to 0.5 wt %);
  f) an Apatite content of from 0.5 wt % to 4 wt % (e.g., from 0.6 wt % to 4 wt %, from 0.8 wt % to 4 wt %, from 1 wt % to 4 wt %);
  g) a Lepidolite content of from 2 wt % to 8 wt % (e.g., from 2.5 wt % to 8 wt %, from 4 wt % to 8 wt %, from 5 wt % to 8 wt %); and/or h) an Amblygonite content of from 0 wt % to 1 wt % (e.g., from 0.1 wt % to 1 wt %, from 0.2 wt % to 1 wt %, from 0.3 wt % to 1 wt %, from 0.5 wt % to 1 wt %).

For instance, the above crushed, refined, ore (or recovered sorted ore) can be present after the first sort in the methods of the present invention (e.g., Grade 1 pieces).

The present invention further relates to a crushed, refined, cesium-containing ore. The refined, crushed ore is characterized by lithium contents below the level where deleterious effects are observed when the refined, crushed ore is refined to yield cesium or rubidium or compounds of cesium or rubidium, and fluids containing such compounds. For instance, the crushed, refined, cesium-containing ore can have the following (based on the weight of the ore):
  a) an optional pollucite and/or nanpingite and/or carnallite content in an amount of from 0 wt % to 15 wt %;
  b) a $Cs_2O$ content of from 0.2 wt % to 6 wt %;
  c) total phosphate mineral content of from 0.1 wt % to 3 wt %;
  d) a % $Cs_2O$: % $P_2O_5$ weight ratio of from 0.1:1 to 15:1;
  e) a $Li_2O$ content of from 0.2 wt % to 2 wt %;
  f) a $Rb_2O$ content of from 0.5 wt % to 4 wt % (e.g., 0.6 wt % to 4 wt %, 0.8 wt % to 2.5 wt %, 1 wt % to 2.5 wt %, 1.5 wt % to 3.5 wt %); and
  g) an average crushed ore size of from 0.1 inch to 3 inches, (e.g., 0.1 inch to 2.5 inches, 0.25 inch to 3 inches, 0.5 inch to 3 inches, 0.75 inch to 2.5 inches, 1 inch to 2.5 inches), wherein all wt % are based on weight of purified ore.

The crushed, refined, cesium containing ore can additionally have one or more of the following (based on the weight of the ore):
  a) a SQUI content in an amount of from 2 wt % to 18 wt % (e.g., from 3 wt % to 15 wt %, from 5 wt % to 15 wt %, from 6 wt % to 10 wt %, from 3 wt % to 10 wt %, from 7 wt % to 10 wt %);
  b) a quartz content in an amount of from 1 wt % to 10 wt % (e.g., from 2 wt % to 10 wt %, from 3 wt % to 10 wt %, from 4 wt % to 10 wt %, from 5 wt % to 10 wt %, from 6 wt % to 10 wt %);

c) a total Feldspar content of from 20 wt % to 70 wt % (e.g., from 25 wt % to 70 wt %, from 30 wt % to 70 wt %, from 35 wt % to 70 wt %, from 40 wt % to 70 wt %, from 50 wt % to 70 wt %);

d) an Albite content of from 0 wt % to 2 wt % (e.g., from 0.1 wt % to 2 wt %, from 0.3 wt % to 2 wt %, from 0.5 wt % to 2 wt %, from 1 wt % to 2 wt %, from 0.75 wt % to 1.5 wt %);

e) an Amphibolite content of from 0.5 wt % to 10 wt % (e.g., from 0.75 wt % to 10 wt %, from 1 wt % to 10 wt %, from 2 wt % to 10 wt %, from 3 wt % to 10 wt %, from 3 wt % to 7 wt %);

f) an Apatite content of from 0 wt % to 1 wt % (e.g., from 0.1 wt % to 1 wt %, from 0.2 wt % to 1 wt %, from 0.3 wt % to 1 wt %, from 0.4 wt % to 1 wt %, from 0.5 wt % to 1 wt %);

g) a Lepidolite content of from 0.5 wt % to 15 wt % (e.g., from 0.75 wt % to 15 wt %, from 1 wt % to 15 wt %, from 2 wt % to 15 wt %, from 5 wt % to 15 wt %, from 7 wt % to 15 wt %); and/or h) an Amblygonite content of from 0.1 wt % to 3 wt % (e.g., from 0.2 wt % to 3 wt %, from 0.5 wt % to 3 wt %, from 1 wt % to 3 wt %, from 0.75 wt % to 2.5 wt %, from 1 wt % to 2 wt %).

The above crushed, refined ore (or recovered sorted ore) can be formed or present from combining the first sort with the second sort (e.g., a combination of the Grade 1 pieces with the Grade 2A pieces). The present invention further relates to this combination. The first sort can comprise 20 wt % to 75 wt % of the combined sort, such as 25 wt % to 70 wt %, 30 wt % to 60 wt %, and the like, and the remaining wt % can be the second sort.

The present invention further relates to a solution containing a cesium containing compound formed from or containing one or more of the purified ores mentioned herein.

Representative examples of solutions containing a cesium containing compound formed from or containing one or more of the purified ores are described below. Two of the cesium salt solutions illustrated below reflect the processing of two of the purified ore streams. The first purified ore is a Grade 1 composition. The second purified ore stream reflects a weighted composition of Grade 1 plus Grade 2A streams. For comparison, the third cesium salt solution is constructed from the unpurified secondary ore.

The three comparative alkali formate, oil-field brines presented were made with an uncalcined, sulfuric acid based extraction process.

Using Grade 1 pieces (Fluid A), a fully saturated brine with the following composition was prepared from the ore (percents by weight of fluid):
Cesium Formate: 78.54 wt %
Lithium Formate: 0.51 wt %
Sodium Formate: 0.95 wt %
Rubidium Formate: 0.56 wt %
Potassium Formate: 0.43 wt %
Water Content: 19.02 wt %.

Using combined Grade 1&2A pieces (Fluid B), a fully saturated brine with the following composition was prepared from the ore (percents by weight of fluid):
Cesium Formate: 69.25 wt %
Lithium Formate: 1.10 wt %
Sodium Formate: 2.07 wt %
Rubidium Formate: 1.73 wt %
Potassium Formate: 3.00 wt %
Water Content: 22.84 wt %.

Using unsorted secondary ore (Fluid C), a fully saturated brine with the following composition was prepared from the ore (percents by weight of fluid):
Cesium Formate: 48.43 wt %
Lithium Formate: 4.04 wt %
Sodium Formate: 4.14 wt %
Rubidium Formate: 1.66 wt %
Potassium Formate: 4.47 wt %
Water Content: 37.27 wt %.

The alkali formate solutions Fluid A and Fluid B generated from sorted, purified ore fractions were capable of sustaining stable, high specific gravity, solids free, oil-field brines. The unpurified secondary ore processed into Fluid C was incapable of sustaining the required saturation weight to yield a useful specific gravity. There is an insufficient weight percentage of soluble cesium formate present. Too much water was required for alkali saturation to achieve desired solution densities (over 2.0 SG and preferably over 2.1 SG) for brine stability. Also for perspective, the lithium fraction for this stream alone, viewed as a separate saturated entity, would represent a 25% aqueous based salt solution. For purposes of the present invention, SG is measured/normalized at a temperature 15.6 deg C.

Formate-containing oil-field brine solutions are commonly buffered with soluble carbonate/bicarbonate. This soluble $CO_3$ presence, in concert with a high degree of solution saturation, can further exacerbate formate brine instability by precipitating lithium carbonate, which can further seed and enable formate precipitation.

The present invention will be further clarified by the following examples, which are intended to be exemplary of the present invention.

EXAMPLES

Example 1

In this example, a 789 kg quantity of secondary ore mined from Tanco granitic pegmatite at Bernic Lake, Manitoba, Canada was recovered. The secondary ore (with a U.S. mesh size of +5 inch) had an estimated pollucite content of 45.72 wt % (wherein all wt % unless stated otherwise, are based on the weight of the starting secondary ore). The secondary ore was estimated to have a $Cs_2O$ content of about 9 wt %. The secondary ore also contained Lepidolite, Feldspar, Quartz, SQUI, Amblygonite, and Albite, and minor amounts of other mineral/rock types.

For sorting, a dual energy X-ray transmission (DEXRT) sorter obtained from Commodas Ultrasort, GmbH, Wedel, Germany was used. The feed rate through the sorter was about 5 to 10 ton/hour. The sorter was calibrated using five (5) training sets of rocks from known ores. Each training set had the same mineral types but had a different size fraction. The following five size fractions were used to calibrate the sorter:
−2 inches+1.5 inches
−1.5 inches+1 inch
−1 inch+0.5 inch
−0.5 inch+0.25 inch
−0.25 inch+0.125 inch.

The rock types in each training set were Pollucite, Lepidolite, Feldspar 4, Feldspar 3, Quartz, SQUI, Amblygonite, and Albite. These training sets were passed through the sorter to calibrate the sorter and to determine the scan parameters for atomic number and material density of the Pollucite for each size fraction.

The starting secondary ore was crushed to a particle size such that it passed through a U.S. mesh of −2.5 inches. The crushed ore was then divided into the same five size fractions identified above. Each of the size fractions were fed separately on a belt to the sorter and scanned. A dual energy scan of each individual piece of crushed ore was made and image processing was conducted to generate color images of each individual piece to reflect atomic number and material density. In the first sort, the sorter was set to eject any individual piece that had over 50% by volume of a determined or calculated atomic number of 50 or higher and a material density of from 2.7 to 3.2 g/cm$^3$ from its normal trajectory by air jets as shown in FIG. 2. The ejected pieces were designed as useful, Grade 1 pieces.

Then, the "accept" pieces not ejected from the first sort (the Grade 2 pieces) were collected and then passed through the same sorter. For the second pass, the settings of the sorter were adjusted to eject any individual piece that had over 50% by volume of a determined or calculated atomic number of 30 or higher and a material density of 2.5 to 3.2 g/cm$^3$ from its normal trajectory by air jets to form the second ore stream (Grade 2A pieces).

As can be seen in Table 1 below, in the method of the invention, the amount of Cs$_2$O went from 9 wt % in the starting secondary ore to 19.2 wt % in the first sort, and 3 wt % in the second sort, with an overall low and acceptable phosphate and lithium content satisfactory for used in cesium compounds.

The "Step 1 Ejects" refers to the results of the first sorting, which is also known as the "Grade 1 pieces." Table 1 shows the various weight per size fractions, the weight percent that this represents is based on the overall weight of the first sort and also shows the weight percent Cs$_2$O per size fraction. The various amounts per size fraction, as well as for totals for the first sort with regard to Rb$_2$O, Li$_2$O, Na$_2$O, and K$_2$O are also reflected. Table 1 shows the same data for "Step 2 Ejects," the results of the second sorting, which passed Grade 2 pieces (Step 1 Accepts), through a second sorting step. As can be seen, after the second sorting, the Grade 2A pieces had 3.07 wt % Cs$_2$O, evidence that the first sorting did a very efficient job of recovering the cesium from the secondary ore, and the second sort yielded additional cesium missed by the first sorting. Table 1 further shows the "Step 2 Accepts", the Grade 2B pieces. The percent Cs$_2$O for this remaining amount was significantly lower, at 0.58 wt % of the material in the Grade 2B pieces. Table 1 below further sets forth, by size fraction, the amount of the starting secondary ore, and the percent phosphates, which are highly undesirable minerals that typically contain lithium, which is unwanted in the cesium recoveries. Table 1 shows how the first sorting and second sorting steps recovered low phosphate level material, especially compared to the cesium level, and this is reflected in the Cs:P weight ratio. In this example and all examples here, the % Cs$_2$O, % P$_2$O$_5$, and % Ta$_2$O$_5$ were measured using x-ray fluorescence (XRF) and using fused and pressed pellets. % Rb$_2$O, K$_2$O, Na$_2$O, and Li$_2$O were measured using Inductively Coupled Plasma (ICP) analytical technique. Unless stated otherwise, all other % measurement for the oxides or metals were done using XRF.

TABLE 1

(all % numbers in wt %)

| Size Fraction (inches) | Wt (kg) | Wt % | % Cs$_2$O | % Rb$_2$O | % Li$_2$O | % Na$_2$O | % K$_2$O | % P$_2$O$_5$ | Cs:P (wt ratio) |
|---|---|---|---|---|---|---|---|---|---|
| Step 1 Ejects (First Sort Results - Grade 1 Pieces) | | | | | | | | | |
| −2" + 1½" | 65.80 | 18.24 | 20.50 | 1.19 | 0.95 | 1.42 | 1.45 | 0.64 | 32.04 |
| −1½" + 1" | 60.90 | 16.89 | 24.36 | 1.53 | 0.71 | 1.61 | 1.26 | 0.35 | 68.93 |
| −1" + ½" | 67.10 | 18.61 | 19.84 | 1.33 | 0.93 | 1.46 | 1.56 | 0.56 | 35.43 |
| −½" + ¼" | 67.85 | 18.81 | 18.56 | 1.27 | 0.89 | 1.51 | 1.62 | 0.95 | 19.53 |
| −¼" + ⅛" | 99.00 | 27.45 | 12.82 | 1.28 | 0.95 | 1.42 | 1.83 | 1.58 | 8.13 |
| Total | 360.65 | 100.00 | 19.22 (avg) | 1.32 (avg) | 0.89 (avg) | 1.48 (avg) | 1.55 (avg) | 0.82 (avg) | 32.81 (avg) |
| Step 2 Ejects (Second Sort Results - Grade 2A Pieces) | | | | | | | | | |
| −2" + 1½" | 18.00 | 19.63 | 1.20 | 0.71 | 1.59 | 1.36 | 4.94 | 0.46 | |
| −1½" + 1" | 16.50 | 17.99 | 3.80 | 0.69 | 1.23 | 1.50 | 5.69 | 0.41 | |
| −1" + ½" | 25.30 | 27.59 | 6.09 | 0.51 | 1.34 | 1.57 | 4.58 | 1.07 | |
| −½" + ¼" | 19.55 | 21.32 | 2.18 | 0.95 | 1.03 | 1.71 | 4.80 | 1.55 | |
| −¼" + ⅛" | 12.35 | 13.47 | 2.10 | 0.99 | 1.09 | 1.37 | 3.08 | 2.29 | |
| Total | 91.70 | 100.00 | 3.07 (avg) | 0.77 (avg) | 1.26 (avg) | 1.50 (avg) | 4.62 (avg) | 1.15 (avg) | |
| Step 2 Accepts (Remaining Material - Grade 2B Pieces) | | | | | | | | | |
| −2" + 1½" | 80.30 | 23.86 | 0.23 | 0.08 | 2.36 | 2.32 | 0.46 | 3.75 | |
| −1½" + 1" | 84.70 | 25.17 | 0.31 | 0.07 | 2.76 | 1.64 | 0.44 | 5.77 | |
| −1" + ½" | 81.00 | 24.07 | 0.62 | 0.08 | 2.27 | 1.78 | 0.59 | 3.35 | |
| −½" + ¼" | 58.10 | 17.26 | 0.55 | 0.06 | 1.83 | 1.45 | 0.45 | 3.99 | |
| −¼" + ⅛" | 32.45 | 9.64 | 1.21 | 0.11 | 1.43 | 1.27 | 0.82 | 3.44 | |
| Total | 336.55 | 100.00 | 0.58 (avg) | 0.08 (avg) | 2.13 (avg) | 1.69 (avg) | 0.55 (avg) | 4.06 (avg) | |
| Starting Feedstock (Starting Secondary Ore) | | | | | | | | | |
| −2" + 1½" | 164.10 | 20.80 | 8.47 | 0.59 | 1.71 | 1.85 | 1.35 | 2.14 | |
| −1½" + 1" | 162.10 | 20.55 | 9.70 | 0.68 | 1.83 | 1.61 | 1.28 | 3.19 | |
| −1" + ½" | 173.40 | 21.98 | 8.86 | 0.63 | 1.62 | 1.63 | 1.55 | 1.94 | |

TABLE 1-continued (all % numbers in wt %)

| Size Fraction (inches) | Wt (kg) | Wt % | % $Cs_2O$ | % $Rb_2O$ | % $Li_2O$ | % $Na_2O$ | % $K_2O$ | % $P_2O_5$ | Cs:P (wt ratio) |
|---|---|---|---|---|---|---|---|---|---|
| $-\frac{1}{2}'' + \frac{1}{4}''$ | 145.50 | 18.44 | 9.17 | 0.74 | 1.28 | 1.51 | 1.58 | 2.25 | |
| $-\frac{1}{4}'' + \frac{1}{8}''$ | 143.80 | 18.23 | 9.28 | 0.99 | 1.07 | 1.38 | 1.71 | 2.06 | |
| Total | 788.90 | 100.00 | 9.09 (avg) | 0.73 (avg) | 1.50 (avg) | 1.60 (avg) | 1.49 (avg) | 2.31 (avg) | |

Example 2

In this example, the same procedures as in Example 1 were repeated, but with a different starting secondary ore to show the ability of the sorting techniques to process different cesium contents in the starting secondary ore. Also, different size fractions were used to calibrate and to sort. The results are set forth below in Table 2. In this example, besides the indicated mesh screen for size fraction, a bar screen was also used to allow rocks with a larger single dimension, for instance in length, to pass through and be processed. In Table 2 the first entry under Step 1 Ejects is crushed ore which would not pass through a 50 mm mesh screen which was passed through a 60 mm bar screen and collected on a 40 mm bar screen. Essentially, this was the bar screen fraction between 40 mm and 60 mm, which cannot pass through a 50 mm mesh screen. Typically this type of material has one dimension that is larger than 50 mm, but has remaining dimensions that are smaller than 50 mm and is sortable material using the technology of the present invention. The second entry in Table 2 under Step 1 Ejects refers to material that would not pass through a 50 mm mesh screen, but passes through a 40 mm bar screen. As seen in the data, the starting $Cs_2O$ content for the starting secondary ore was 4.65 wt % based on the weight of the starting secondary ore. After the first sorting, the amount of cesium ($Cs_2O$) in the first sort by weight was about 21 wt % $Cs_2O$, which was an incredible and surprising increase in the purity of the cesium in the first sort compared to the starting cesium content. The remaining recovery amounts are set forth in Table 2.

As a result of the first sort, the ejects (Grade 1 pieces) had the following make-up (based on the weight of the first sorted rocks (Grade 1 pieces)):

a) pollucite content in an amount of 67.1 wt %;
b) a $Cs_2O$ content of 21.3 wt %;
c) total phosphate mineral content of 0.49 wt %;
d) a % $Cs_2O$: % $P_2O_5$ weight ratio of at least 43.7:1;
e) a $Li_2O$ content of 0.9 wt %;
f) a $Rb_2O$ content of 0.88 wt %.

The first sort had a mineral content of:
a) a SQUI content in an amount of 0.4 wt %;
b) a quartz content in an amount of 0.8 wt %;
c) a total Feldspar content of 3.26 wt %;
d) an Albite content of 0 wt %;
e) an Amphibolite content of 0.4 wt %;
f) an Apatite content of 1.26 wt %;
g) a Lepidolite content of 2.24 wt %; and
h) an Amblygonite content of 0.4 wt %.

As a result of the second sort, the ejects (Grade 2A pieces) had the following make-up (based on the weight of the second sorted rocks (Grade 2A pieces)):

a) pollucite content in an amount of 0 wt %;
b) a $Cs_2O$ content of 3 wt %;
c) total phosphate mineral content of 0.79 wt %;
d) a % $Cs_2O$: % $P_2O_5$ weight ratio of 1.34:1;
e) a $Li_2O$ content of 1.06 wt %; and
f) a $Rb_2O$ content of 1.66 wt %

The second sort had a mineral content of:
a) a SQUI content in an amount of 0.17 wt %;
b) a quartz content in an amount of 1.97 wt %;
c) a total Feldspar content of 79.78 wt %;
d) an Albite content of 0 wt %;
e) an Amphibolite content of 2.09 wt %;
f) an Apatite content of 0 wt %;
g) a Lepidolite content of 1.25 wt %; and
h) an Amblygonite content of 0.53 wt %.

TABLE 2

(all % numbers in wt %)

| Size Fraction | Wt (kg) | Wt % | % $Cs_2O$ | % $Rb_2O$ | % $Li_2O$ | % $Na_2O$ | % $K_2O$ | % $P_2O_5$ | Cs:P (wt ratio) |
|---|---|---|---|---|---|---|---|---|---|
| Step 1 Ejects (First Sort Results - Grade 1 Pieces) | | | | | | | | | |
| >#50 mm + ‖ 40 mm − ‖ 60 mm | 175.00 | 22.88 | 21.01 | 0.76 | 1.26 | 1.41 | 1.29 | 0.29 | 71.63 |
| >#50 mm < ‖ 40 mm | 80.00 | 10.46 | 18.37 | 0.74 | 1.32 | 1.52 | 1.40 | 0.30 | 61.93 |
| +25-50 mm | 180.00 | 23.53 | 21.98 | 0.95 | 0.89 | 1.38 | 1.86 | 0.64 | 34.52 |
| +12.5-25 mm | 155.00 | 20.26 | 22.36 | 0.94 | 0.69 | 1.27 | 1.41 | 0.37 | 59.80 |
| +6-12.5 mm | 85.00 | 11.11 | 22.58 | 0.92 | 0.71 | 1.49 | 1.59 | 0.65 | 34.57 |
| +3-6 mm | 90.00 | 11.76 | 19.75 | 0.91 | 0.77 | 1.46 | 1.78 | 0.77 | 25.77 |
| Total | 765.00 | 100.00 | 21.01 (avg) | 0.87 (avg) | 0.94 (avg) | 1.42 (avg) | 1.56 (avg) | 0.50 (avg) | 48.04 (avg) |
| Step 2 Ejects (Second Sort Results - Grade 2A Pieces) | | | | | | | | | |
| >#50 mm + ‖ 40 mm − ‖ 60 mm | 275.00 | 24.44 | 0.74 | 1.62 | 1.47 | 1.40 | 7.51 | 0.47 | |
| >#50 mm < ‖ 40 mm | 140.00 | 12.44 | 0.58 | 1.59 | 1.30 | 1.81 | 7.11 | 0.59 | |
| +25-50 mm | 300.00 | 26.67 | 0.72 | 1.72 | 0.84 | 1.73 | 9.37 | 0.77 | |

TABLE 2-continued (all % numbers in wt %)

| Size Fraction | Wt (kg) | Wt % | % Cs$_2$O | % Rb$_2$O | % Li$_2$O | % Na$_2$O | % K$_2$O | % P$_2$O$_5$ | Cs:P (wt ratio) |
|---|---|---|---|---|---|---|---|---|---|
| +12.5-25 mm | 240.00 | 21.33 | 1.12 | 1.72 | 0.85 | 1.50 | 7.82 | 1.07 | |
| +6-12.5 mm | 120.00 | 10.67 | 2.64 | 1.60 | 0.94 | 1.58 | 7.58 | 1.09 | |
| +3-6 mm | 50.00 | 4.44 | 2.14 | 1.63 | 0.81 | 1.51 | 6.13 | 1.21 | |
| Total | 1125.00 | 100.00 | 1.32 (avg) | 1.65 (avg) | 1.04 (avg) | 1.59 (avg) | 7.59 (avg) | 0.87 (avg) | |
| Step 2 Accepts (Remaining Material - Grade 2B Pieces) | | | | | | | | | |
| >#50 mm + ‖ 40 mm – ‖ 60 mm | 645.00 | 27.22 | 0.26 | 0.40 | 3.22 | 1.22 | 0.49 | 1.50 | |
| >#50 mm < ‖ 40 mm | 265.00 | 11.18 | 0.22 | 0.32 | 3.84 | 1.03 | 0.20 | 3.21 | |
| +25-50 mm | 620.00 | 26.16 | 0.23 | 0.60 | 2.82 | 1.42 | 0.47 | 3.48 | |
| +12.5-25 mm | 415.00 | 17.51 | 0.35 | 0.42 | 2.48 | 1.16 | 0.32 | 3.90 | |
| +6-12.5 mm | 245.00 | 10.34 | 1.17 | 0.45 | 1.98 | 1.38 | 0.82 | 2.85 | |
| +3-6 mm | 180.00 | 7.59 | 1.19 | 0.59 | 1.97 | 1.44 | 1.24 | 2.75 | |
| Total | 2370.00 | 100.00 | 0.57 (avg) | 0.46 (avg) | 2.72 (avg) | 1.27 (avg) | 0.59 (avg) | 2.95 (avg) | |
| Starting Feedstock (Starting Secondary Ore) | | | | | | | | | |
| >#50 mm + ‖ 40 mm – ‖ 60 mm | 1095.00 | 25.70 | 3.70 | 0.76 | 2.47 | 1.29 | 2.38 | 1.05 | |
| >#50 mm < ‖ 40 mm | 485.00 | 11.38 | 3.32 | 0.75 | 2.69 | 1.33 | 2.39 | 1.97 | |
| +25-50 mm | 1100.00 | 25.82 | 3.92 | 0.96 | 1.97 | 1.50 | 3.12 | 2.27 | |
| +12.5-25 mm | 810.00 | 19.01 | 4.79 | 0.90 | 1.65 | 1.28 | 2.75 | 2.39 | |
| +6-12.5 mm | 450.00 | 10.56 | 5.61 | 0.84 | 1.46 | 1.46 | 2.77 | 1.96 | |
| +3-6 mm | 320.00 | 7.51 | 6.56 | 0.84 | 1.45 | 1.46 | 2.15 | 1.95 | |
| Total | 4260.00 | 100.00 | 4.65 (avg) | 0.84 (avg) | 1.95 (avg) | 1.39 (avg) | 2.60 (avg) | 1.93 (avg) | |

Example 3

In this example, the same procedures as in Example 1 were repeated, but with a different starting secondary ore, and different size fractions were used to calibrate and to sort. Table 3 below further summarizes the results from Example 1 (identified as "feed 1" in Table 3) and in Example 2 (identified as "feed 2") in Table 3. "Feed 3" is Example 3. In Table 3, the feed grade is a reference to the weight percent of Cs$_2$O in the starting secondary ore. As can be seen, the starting percent of cesium was 9% or lower. Table 3 further breaks down the starting amount of cesium per size fraction. Table 3 also provides the percent of Cs$_2$O recovery based on the amount of available cesium that was present in the starting secondary ore. For instance, feed 1 shows a 93.4% Cs$_2$O recovery which means that 93.4% of all available cesium oxide (by weight) that was available in the starting secondary ore was recovered by the sorting techniques of the present invention. The reference to wt % recovery is a reference to the weight percent of the first sort and second sort that was recovered as eject 1 and eject 2 (Grade 1 pieces and Grade 2A pieces) and which contained the Cs$_2$O. Referring to feed 1, the combined first and second sort comprised 45.72 wt % of the starting low-yield ore. Put another way, over half of the starting weight of the low-yield ore was discarded and yet the amount of available cesium recovered was 93.4% and the product grade (which is a reference to the percent purity/concentration of the Cs$_2$O) in the final sorted product was 18.56 percent by weight. Thus, referring to feed 1, the final sorted amount had a purity or concentration level of 18.56 wt % which was over a 100% increase from the starting Cs$_2$O concentration. Similar results were seen for feed 2 which had an even lower starting Cs$_2$O amount and yet resulted in a final Cs$_2$O concentration of 21.26%. Feed 3, which is the third example, showed a starting cesium oxide content of 2.72% by weight and yet the finished sorted product had a cesium oxide concentration of 20.66 wt % wherein 92.14 wt % of the available cesium oxide (in the starting ore) was recovered by the sorting techniques.

All of this shows the unexpected and superior ability of the present invention to recover cesium oxide from very low-yield ore to obtain a useful product for cesium applications.

TABLE 3

| Stream | Feed Grade, wt % Cs$_2$O | Cs$_2$O % Recovery | Wt % Recovery | Product Grade (% purity/concentration) |
|---|---|---|---|---|
| feed1 | 9.08 | 93.40 | 45.72 | 18.56 |
| −2″ + 1 ½″ | 8.47 | 97.10 | 40.10 | 20.50 |
| −1 ½″ + 1″ | 9.70 | 94.34 | 37.57 | 24.36 |
| −1″ + ½″ | 8.86 | 86.70 | 38.70 | 19.84 |
| −½″ + ¼″ | 9.17 | 94.40 | 46.63 | 18.56 |
| −¼″ + ⅛″ | 9.28 | 95.12 | 68.85 | 12.82 |
| feed2 | 4.34 | 88.05 | 17.96 | 21.26 |
| >#50 mm + ‖ 40 mm – ‖ 60 mm | 3.70 | 90.83 | 15.98 | 21.01 |
| >#50 mm < ‖ 40 mm | 3.32 | 91.41 | 16.49 | 18.37 |
| +25-50 mm | 3.92 | 91.67 | 16.36 | 21.98 |
| +12.5-25 mm | 4.79 | 89.31 | 19.14 | 22.36 |
| +6-12.5 mm | 5.61 | 76.06 | 18.89 | 22.58 |
| +3-6 mm | 6.56 | 84.72 | 28.13 | 19.75 |
| feed3 | 2.72 | 85.71 | 11.28 | 20.66 |
| >+#60 mm – ‖ 60 mm | 1.73 | 92.14 | 9.23 | 17.23 |
| >#60 mm < ‖ 50 mm | 2.01 | 89.39 | 8.19 | 21.94 |
| +25-50 mm | 3.03 | 92.33 | 13.48 | 20.72 |
| +12.5-25 mm | 3.14 | 80.76 | 10.74 | 23.59 |
| +6-12.5 mm | 3.32 | 75.79 | 10.93 | 23.03 |
| +3-6 mm | 3.38 | 76.64 | 17.87 | 14.49 |

The present invention includes the following aspects/embodiments/features in any order and/or in any combination:

1. A method to recover cesium, rubidium, or both from secondary ore, wherein said secondary ore comprises 25 wt % Cs$_2$O or less based on overall weight of said secondary ore and the majority of said secondary ore comprise pieces having at least one dimension that is over 5 inches (12.7 cm), said method comprising:

a) obtaining crushed ore and/or b) crushing said secondary ore to obtain crushed ore, said crushed ore comprising individual pieces, each individual piece having a size capable of passing through a U.S. standard sieve mesh/screen opening of 5 inches, such as 4 inches or 3 inches (76.2 mm);

passing said crushed ore through a first sorter to conduct a first sorting at a feed rate of at least 1 ton/hour, wherein said first sorter determines whether each individual piece of crushed ore is a "Grade 1 piece" or "Grade 2 piece", based on said first sorter conducting at least one scan of each individual piece and determining or calculating atomic number or material density or both of each individual piece, wherein said "Grade 1 piece" comprises $Cs_2O$, or $Cs_2O$ and $Rb_2O$ together, in an amount of at least 20% based on the weight of said individual piece;

separating said Grade 1 pieces from said Grade 2 pieces, whereby wt % $Cs_2O$ of said Grade 1 pieces is at least 10% by weight higher than wt % $Cs_2O$ in said secondary ore.

2. The method of any preceding or following embodiment/feature/aspect, further comprising extracting cesium, rubidium or both by subjecting said Grade 1 pieces to at least one acid treatment.

3. The method of any preceding or following embodiment/feature/aspect, wherein said secondary ore comprises 20 wt % $Cs_2O$ or less.

4. The method of claim 1, wherein said secondary ore comprises 15 wt % $Cs_2O$ or less.

5. The method of any preceding or following embodiment/feature/aspect, wherein said secondary ore comprises 10 wt % $Cs_2O$ or less.

6. The method of any preceding or following embodiment/feature/aspect, wherein said secondary ore comprises 1 wt % to 15 wt % $Cs_2O$.

7. The method of any preceding or following embodiment/feature/aspect, wherein said secondary ore comprises 1 wt % to 10 wt % $Cs_2O$.

8. The method of any preceding or following embodiment/feature/aspect, wherein said secondary ore comprises 0.25 wt % to 5 wt % $Cs_2O$.

9. The method of any preceding or following embodiment/feature/aspect, further comprising calcining said Grade 1 pieces after said separating.

10. The method of any preceding or following embodiment/feature/aspect, further comprising calcining said Grade 1 pieces after said separating at a calcining temperature of from about 800 deg C to about 1200 deg C.

11. The method of any preceding or following embodiment/feature/aspect, wherein said secondary ore comprises pollucite.

12. The method of any preceding or following embodiment/feature/aspect, wherein said secondary ore comprises at least 1 wt % pollucite based on the weight of said secondary ore.

13. The method of any preceding or following embodiment/feature/aspect, wherein said secondary ore comprises 1 to 5 wt % pollucite based on the weight of said secondary ore.

14. The method of any preceding or following embodiment/feature/aspect, wherein said secondary ore comprises at least 3 wt % pollucite based on the weight of said secondary ore.

15. The method of any preceding or following embodiment/feature/aspect, wherein said first sorter detects and selects said Grade 1 piece based on a calculated or determined atomic number of at least 80.

16. The method of any preceding or following embodiment/feature/aspect, wherein said first sorter is detects and selects said Grade 1 piece based on a calculated or determined atomic number of at least 90.

17. The method of any preceding or following embodiment/feature/aspect, wherein said first sorter detects and selects said Grade 1 piece based on a calculated or determined atomic number of at least 100.

18. The method of any preceding or following embodiment/feature/aspect, wherein said first sorter detects and selects said Grade 1 piece based on a calculated or determined atomic number of from 80 to 150.

19. The method of any preceding or following embodiment/feature/aspect, wherein said method captures at least about 40% by weight of available $Cs_2O$ present in said secondary ore.

20. The method of any preceding or following embodiment/feature/aspect, wherein said method captures at least about 50% by weight of available $Cs_2O$ present in said secondary ore.

21. The method of any preceding or following embodiment/feature/aspect, wherein said method captures at least about 10% by weight of available $Rb_2O$ present in said secondary ore.

22. The method of any preceding or following embodiment/feature/aspect, wherein said method captures at least about 15% by weight of available $Rb_2O$ present in said secondary ore.

23. The method of any preceding or following embodiment/feature/aspect, wherein said at least one acid treatment comprises mixing said Grade 1 pieces with concentrated sulfuric acid.

24. The method of any preceding or following embodiment/feature/aspect, wherein said at least one acid treatment comprises mixing said Grade 1 pieces with acid in an acid:cesium weight ratio that exceeds 4:1.

25. The method of any preceding or following embodiment/feature/aspect, further comprising a second sorting step comprising passing said Grade 2 pieces through a second sorter, which is the same or different from said first sorter, wherein said second sorter determines whether each individual piece of said Grade 2 pieces is a "Grade 2A piece" or "Grade 2B piece", based on said second sorter conducting at least one scan of each individual piece and determining or calculating an effective atomic number or material density or both of each individual piece, wherein said "Grade 2A piece" comprises $Rb_2O$ in an amount of at least 20% based on the weight of said individual piece, and then separating said Grade 2A pieces from said Grade 2B pieces.

26. The method of any preceding or following embodiment/feature/aspect, wherein said second sorter is set such that said Grade 2A piece is determined based on a calculated or determined atomic number of at least 50.

27. The method of any preceding or following embodiment/feature/aspect, wherein said second sorter is set such that said Grade 1 piece is determined based on a calculated or determined atomic number of at least 60.

28. The method of any preceding or following embodiment/feature/aspect, wherein said second sorter is set such that said Grade 1 piece is determined based on a calculated or determined atomic number of at least 70.

29. The method of any preceding or following embodiment/feature/aspect, wherein said second sorter is set such that said Grade 1 piece is determined based on a calculated or determined atomic number of from 60 to 150.

30. The method of any preceding or following embodiment/feature/aspect, wherein said second sorting captures at least about 10% by weight of available $Cs_2O$ present in said secondary ore, based on weight of said secondary ore at start.
31. The method of any preceding or following embodiment/feature/aspect, wherein said second sorting captures at least about 15% by weight of available $Cs_2O$ present in said secondary ore, based on weight of said secondary ore at start.
32. The method of any preceding or following embodiment/feature/aspect, wherein said second sorting captures at least about 20% by weight of available $Cs_2O$ present in said secondary ore, based on weight of said secondary ore at start.
33. The method of any preceding or following embodiment/feature/aspect, wherein said second sorting captures at least about 20% by weight of available $Rb_2O$ present in said secondary ore, based on weight of said secondary ore at start.
34. The method of any preceding or following embodiment/feature/aspect, wherein said second sorting captures at least about 30% by weight of available $Rb_2O$ present in said secondary ore, based on weight of said secondary ore at start.
35. The method of any preceding or following embodiment/feature/aspect, wherein said second sorting captures at least about 40% by weight of available $Rb_2O$ present in said secondary ore, based on weight of said secondary ore at start.
36. The method of any preceding or following embodiment/feature/aspect, wherein said second sorting captures at least about 65% by weight of available $Rb_2O$ present in said secondary ore, based on weight of said secondary ore at start.
37. The method of any preceding or following embodiment/feature/aspect, wherein said first sorting and said second sorting combined capture at least 60% by weight of available $Cs_2O$ present in said secondary ore, based on weight of said secondary ore at start.
38. The method of any preceding or following embodiment/feature/aspect, wherein said first sorting and said second sorting combined capture at least 70% by weight of available $Cs_2O$ present in said secondary ore, based on weight of said secondary ore at start.
39. The method of any preceding or following embodiment/feature/aspect, wherein said first sorting and said second sorting combined capture at least 85% by weight of available $Cs_2O$ present in said secondary ore, based on weight of said secondary ore at start.
40. The method of any preceding or following embodiment/feature/aspect, wherein said first sorting and said second sorting combined capture at least 40% by weight of available $Rb_2O$ present in said secondary ore, based on weight of said secondary ore at start.
41. The method of any preceding or following embodiment/feature/aspect, wherein said first sorting and said second sorting combined capture at least 50% by weight of available $Rb_2O$ present in said secondary ore, based on weight of said secondary ore at start.
42. The method of any preceding or following embodiment/feature/aspect, wherein said first sorting and said second sorting combined capture at least 60% by weight of available $Rb_2O$ present in said secondary ore, based on weight of said secondary ore at start.
43. The method of any preceding or following embodiment/feature/aspect, wherein said first sorting and said second sorting combined capture at least 65% by weight of available $Rb_2O$ present in said secondary ore, based on weight of said secondary ore at start.
44. The method of any preceding or following embodiment/feature/aspect, wherein said first sorting and said second sorting combined capture at least 60% by weight of available $Cs_2O$ present in said secondary ore, based on weight of said secondary ore at start, and at least 40% by weight of available $Rb_2O$ present in said secondary ore, based on weight of said secondary ore at start.
45. The method of any preceding or following embodiment/feature/aspect, wherein said first sorting and said second sorting combined capture at least 70% by weight of available $Cs_2O$ present in said secondary ore, based on weight of said secondary ore at start, and at least 50% by weight of available $Rb_2O$ present in said secondary ore, based on weight of said secondary ore at start.
46. The method of any preceding or following embodiment/feature/aspect, wherein said first sorting and said second sorting combined capture at least 80% by weight of available $Cs_2O$ present in said secondary ore, based on weight of said secondary ore at start, and at least 60% by weight of available $Rb_2O$ present in said secondary ore, based on weight of said secondary ore at start.
47. The method of any preceding or following embodiment/feature/aspect, wherein said Grade 1 pieces comprise at least 100% more $Cs_2O$ based on a comparison of weight percent of $Cs_2O$ in secondary ore to weight percent of $Cs_2O$ in Grade 1 pieces.
48. The method of any preceding or following embodiment/feature/aspect, wherein said Grade 1 pieces comprise at least 150% more $Cs_2O$ based on a comparison of weight percent of $Cs_2O$ in secondary ore to weight percent of $Cs_2O$ in Grade 1 pieces.
49. The method of any preceding or following embodiment/feature/aspect, wherein said Grade 1 pieces comprise at least 200% more $Cs_2O$ based on a comparison of weight percent of $Cs_2O$ in secondary ore to weight percent of $Cs_2O$ in Grade 1 pieces.
50. The method of any preceding or following embodiment/feature/aspect, wherein said Grade 1 pieces comprise at least 300% more $Cs_2O$ based on a comparison of weight percent of $Cs_2O$ in secondary ore to weight percent of $Cs_2O$ in Grade 1 pieces.
51. The method of any preceding or following embodiment/feature/aspect, further comprising extracting cesium, rubidium or both by subjecting said Grade 2A pieces to at least one non-acid treatment.
52. The method of any preceding or following embodiment/feature/aspect, wherein said at least one non-acid treatment comprises crushing, calcining, or both.
53. The method of any preceding or following embodiment/feature/aspect, wherein said secondary ore comprises rhodozite, pezzottaite, borate ramanite, beryls, cesstibtantite, avogadrite, margaritasite, kupletskite, nalivkinite, londonite, or any combinations thereof.
54. The method of any preceding or following embodiment/feature/aspect, wherein said secondary ore comprises rubicline, borate ramanite, voloshonite, or any combinations thereof.
55. The method of any preceding or following embodiment/feature/aspect, wherein said crushing said secondary ore to obtain crushed ore comprising individual pieces, each individual piece having a size capable of passing through a U.S. standard sieve mesh/screen opening of 2 inches (50.8 mm).

56. The method of any preceding or following embodiment/feature/aspect, wherein said crushing said secondary ore to obtain crushed ore comprising individual pieces, each individual piece having a size capable of passing through a mesh/screen of 1 inch.
57. The method of any preceding or following embodiment/feature/aspect, wherein said crushing said secondary ore to obtain crushed ore comprising individual pieces, each individual piece having a size capable of passing through a mesh/screen of 0.5 inch.
58. The method of any preceding or following embodiment/feature/aspect, wherein said crushing said secondary ore to obtain crushed ore comprising individual pieces, each individual piece having a size capable of passing through a mesh/screen of 0.25 inch.
59. The method of any preceding or following embodiment/feature/aspect, wherein said crushing said secondary ore to obtain crushed ore comprising individual pieces, each individual piece having a size capable of passing through a mesh/screen of 0.1 inch.
60. A refined crushed ore in the form of mineral rocks comprising:
    a) a cesium bearing rock content in an amount of from 10 wt % to 90 wt %, wherein said cesium bearing rock is pollucite, nanpingite, and/or carnallilte;
    b) a $Cs_2O$ content of from 5 wt % to 32 wt %;
    c) total phosphate mineral content of from 1 wt % to 10 wt %;
    d) a % $Cs_2O$: % $P_2O_5$ weight ratio of at least 4:1;
    e) a $Li_2O$ content of from 0.59 wt % to 1.5 wt %;
    f) a $Rb_2O$ content of from 0.5 wt % to 1.8 wt %; and
    g) an average crushed ore size of from 0.1 inch to 5 inches such as 0.1 to 2.5 inches, wherein all wt % are based on weight of refined crushed ore.
61. The refined crushed ore of any preceding or following embodiment/feature/aspect, further comprising at least one of the following:
    a) a SQUI content in an amount of from 0.5 wt % to 5 wt %;
    b) a quartz content in an amount of from 0.5 wt % to 5 wt %;
    c) a total Feldspar content of from 1 wt % to 10 wt %;
    c) an Albite content of from 0 wt % to 1 wt %;
    d) an Amphibolite content of from 0.1 wt % to 0.5 wt %;
    e) an Apatite content of from 0.5 wt % to 4 wt %;
    f) a Lepidolite content of from 2 wt % to 8 wt %; and/or
    g) an Amblygonite content of from 0 wt % to 1 wt %.
62. The refined crushed ore of any preceding or following embodiment/feature/aspect, wherein said refined crushed ore is obtained in industrial lots of at least 100 lbs (45.4 kg).
63. The refined crushed ore of any preceding or following embodiment/feature/aspect, wherein said refined crushed ore is from a single ore deposit.
64. The method of any preceding or following embodiment/feature/aspect, wherein said first sorter is set such that Grade 1 piece is determined based on a calculated or determined density of at least 2.5 $g/cm^3$.
65. The method of any preceding or following embodiment/feature/aspect, wherein said first sorter is set such that Grade 1 piece is determined based on a calculated or determined density of at least 2.75 $g/cm^3$.
66. The method of any preceding or following embodiment/feature/aspect, wherein said first sorter is set such that Grade 1 piece is determined based on a calculated or determined density of at least 2.8 $g/cm^3$.
67. The method of any preceding or following embodiment/feature/aspect, wherein said first sorter is set such that Grade 1 piece is determined based on a calculated or determined density of a range of from 2.5 $g/cm^3$ to 3.5 $g/cm^3$.
68. The method of any preceding or following embodiment/feature/aspect, wherein said first sorter is set such that Grade 1 piece is determined based on a calculated or determined density of a range of from 2.7 $g/cm^3$ to 3.2 $g/cm^3$.
69. The method of any preceding or following embodiment/feature/aspect, wherein said first sorter conducts at least 2 scans of each individual piece, wherein one scan determines or calculates or estimates atomic number and the other scan determines or calculates or estimates density.
70. The method of any preceding or following embodiment/feature/aspect, wherein said second sorter is set such that Grade 2A piece is determined based on a determined or calculated density of at least 2.5.
71. The method of any preceding or following embodiment/feature/aspect, wherein said second sorter is set such that Grade 2A piece is determined based on determined or calculated density of at least 2.75.
72. The method of any preceding or following embodiment/feature/aspect, wherein said second sorter is set such that Grade 2A piece is determined based on determined or calculated density of at least 2.8.
73. The method of any preceding or following embodiment/feature/aspect, wherein said second sorter is set such that Grade 2A piece is determined based on determined or calculated density of at least 2.9.
74. The method of any preceding or following embodiment/feature/aspect, wherein said second sorter is set such that Grade 2A piece is determined based on calculated or determined density of a range of from 2.8 to 3.3.
75. The method of any preceding or following embodiment/feature/aspect, wherein second sorter is set such that said Grade 2A is determined based on a calculated or determined atomic number and a calculated or determined density.
76. The method of any preceding or following embodiment/feature/aspect, wherein second sorter is set such that said Grade 2A is determined based on a calculated or determined atomic number of at least 30 and a calculated or determined density of at least 2.5.
77. The method of any preceding or following embodiment/feature/aspect, wherein said crushed ore is separated into two or more size fractions that are different from each other and wherein each size fraction is separately passed through said first sorter.
78. The method of any preceding or following embodiment/feature/aspect, said method further comprising, an initial calibration step, wherein before said passing of said crushed ore through said first sorter, passing through two or more size fractions of known rocks and minerals that are representative of the rocks and minerals in said secondary ore to be sorted so as to calibrate said first sorter, for each size fraction, with respect to what is representative of a "Grade 1 piece" or what is representative of a "Grade 2 piece" or both based on scanned properties of atomic number or density or both.
79. The method of any preceding or following embodiment/feature/aspect, wherein said "Grade 1 piece" is determined based on being within 10% of the scanned property of atomic number or density or both for the representative Grade 1 piece for that size fraction.
80. The method of any preceding or following embodiment/feature/aspect, wherein said acid treating comprising subjecting said Grade 1 pieces to sulfuric acid having at least 35% $H_2SO_4$ by weight.

81. The method of any preceding or following embodiment/feature/aspect, wherein said acid treatment is at a temperature of 90 deg C or higher.
82. The method of any preceding or following embodiment/feature/aspect, wherein said acid treatment occurs for at least 15 minutes.
83. The method of any preceding or following embodiment/feature/aspect, said method further comprising subjecting said Grade 1 pieces to comminution to reduce the sizes of the Grade 1 pieces.
84. The method of any preceding or following embodiment/feature/aspect, wherein said secondary ore comprises pollucite, nanpingite, carnallite, petalite, spodumene, lepidolite, biotite, mica, muscovite, feldspar, microcline, rhodozite, Li-muscovite, lithiophilite, amblygonite, illite, cookeite, albite, analcime, squi, amphiboles, pezzottaite, borate ramanite, beryl, cesstibtantite, avogadrite, margaritasite, kupletskite, nalivkinite, londonite, rubicline, and/or voloshonite, or any combinations thereof.
85. The method of any preceding or following embodiment/feature/aspect, wherein said secondary ore comprises pollucite, nanpingite, carnallite, rhodozite, pezzottaite, rubicline, borate ramanite, beryls, voloshonite, cesstibtantite, avogadrite, margaritasite, kupletskite, nalivkinite, petalite, spodumene, lepidolite, biotite, mica, muscovite, feldspar, microcline, Li-muscovite, lithiophilite, amblygonite, illite, cookeite, albite, analcime, squi, amphiboles, lithian mica, amphibolite, lithiophospahe, apatite and/or londonite, or any combinations thereof
86. The method of any preceding or following embodiment/feature/aspect, wherein the Grade 1 pieces are capable of being converted into an oil field alkali formate brine product having a stable 2.3 SG.
87. The method of any preceding or following embodiment/feature/aspect, wherein the Grade 2A pieces combined with the Grade 1 pieces are capable of being converted into an oil field alkali formate brine product having a stable 2.2 SG.
88. The method of any preceding or following embodiment/feature/aspect, wherein the secondary ore is incapable of being converted into an oil field alkali formate brine product having a stable 2.1 SG or higher.
89. The method of any preceding or following embodiment/feature/aspect, wherein the Grade 2B pieces are incapable of being converted into an oil field alkali formate brine product having a stable 2.1 SG or higher.
90. A method to recover cesium, rubidium, potassium, or combinations thereof, from secondary ore, wherein said secondary ore comprises 10% $Cs_2O$, or less, or comprises a total Alkali Oxide ($M_2O$) content of 10% $M_2O$, or less, each respectively based on overall weight of said secondary ore and the majority of said secondary ore comprise pieces having at least one dimension that is over 5 inches, said method comprising:

crushing (or obtaining) said secondary ore to obtain crushed ore comprising individual pieces, each individual piece having a size capable of passing through a mesh/screen of 3 inches;

passing said crushed ore through said first sorter to conduct a first sorting at a feed rate of at least 1 ton/hour, wherein said first sorter determines whether each individual piece of crushed ore is a "Grade 1 piece" or "Grade 2 piece", based on said first sorter conducting at least one scan of each individual piece and determining or calculating atomic number and/or material density of each individual piece, wherein said "Grade 1 piece" comprises $Cs_2O$ in an amount and concentration, each by weight, of at least twice that present in said secondary ore, or, in an amount and concentration, each by weight, of at least twice that present in the "Grade 2 piece".

91. The method of any preceding or following embodiment/feature/aspect, wherein said Grade 1 pieces are subjected to further comminution to any nominal sizing, including finer sizes of less than 100 microns.
92. The method of any preceding or following embodiment/feature/aspect, wherein said secondary ore comprises 6.5 wt % pollucite or less, or 4.8 wt % or less, or 3.2 wt % or less, or from 0.3 wt % to 5 wt % or from 0.3 wt % to 3.2 wt % or from 0.08 wt % to 1.6 wt % pollucite, based on the total weight of the secondary ore.
93. The method of any preceding or following embodiment/feature/aspect, further comprising a second sorting comprising passing said Grade 2 pieces through a second sorter, which is the same or different from said first sorter, wherein said second sorter determines whether each individual piece of said Grade 2 pieces is a "Grade 2A piece" or "Grade 2B piece", based on said second sorter conducting at least one scan of each individual piece and determining or calculating an effective atomic number of each individual piece, wherein said "Grade 2A piece" comprises $Rb_2O$ in an amount and concentration, each by weight, of at least twice that present in said Grade 2 piece, or, in an amount and concentration, each by weight, of at least twice that present in the "Grade 2B piece."
94. The method of any preceding or following embodiment/feature/aspect, wherein the weight recovery can be defined by the $Cs_2O$ and $Rb_2O$ recovery by weight compared to the starting secondary (e.g., Grade 1 pieces based on weight secondary ore), and/or can be compared to the sorted ore (e.g., Grade 2A pieces based on weight of Grade 2 pieces). So, for instance, the $Cs_2O$ recovery (in the Grade 2A pieces) can range from about 5 to about 13 wt % of the total weight of the secondary ore. The $Cs_2O$ recovery (in the Grade 2A pieces) can range from about 30 wt % to 65 wt % based on the weight of the Grade 2 pieces. The $Rb_2O$ recovery (in the Grade 2A pieces) can range from about 30 to about 61 wt % recovery based on the weight of the secondary ore. The $Rb_2O$ recovery (in the Grade 2A pieces) can range from about 43 wt % to about 73 wt % based on the weight of the Grade 2 pieces.
95. The method of any preceding or following embodiment/feature/aspect, wherein said second sorting captures at least about 30% by weight of available $Cs_2O$ present in said Grade 2 pieces, based on weight of said Grade 2 pieces from the first sort.
96. The method of any preceding or following embodiment/feature/aspect, wherein said second sorting captures at least about 50% by weight of available $Cs_2O$ present in said Grade 2 pieces, based on weight of said Grade 2 pieces from the first sort.
97. The method of any preceding or following embodiment/feature/aspect, wherein said second sorting captures at least about 70% by weight of available $Cs_2O$ present in said Grade 2 pieces, based on weight of said Grade 2 pieces from the first sort.
98. The method of any preceding or following embodiment/feature/aspect, wherein said second sorting captures at least about 35% by weight of available $Rb_2O$ present in said Grade 2 pieces, based on weight of said Grade 2 pieces from the first sort.
99. The method of any preceding or following embodiment/feature/aspect, wherein said second sorting captures at least about 50% by weight of available $Rb_2O$ present in said Grade 2 pieces, based on weight of said Grade 2 pieces from the first sort.

100. The method of any preceding or following embodiment/feature/aspect, wherein said second sorting captures at least about 65% by weight of available $Rb_2O$ present in said Grade 2 pieces, based on weight of said Grade 2 pieces from the first sort.

101. The method of any preceding or following embodiment/feature/aspect, wherein said second sorting captures at least about 80% by weight of available $Rb_2O$ present in said Grade 2 pieces, based on weight of said Grade 2 pieces from the first sort.

102. The method of any preceding or following embodiment/feature/aspect, wherein said secondary ore contains minerals, wherein cesium is present as an, in kind, like substitute, such as those contained in ore bodies comprising petalite, spodumene, lepidolite, biotite, mica, muscovite, feldspar, microcline, beryl, Li-muscovite, lithiophilite, amblygonite, illite, cookeite, albite, analcime, squi, amphiboles and/or other mineral mentioned throughout, or any combinations thereof.

103. The method of any preceding or following embodiment/feature/aspect, wherein said secondary ore contains minerals, where rubidium is present as an, in kind, like substitute, such as those contained in ore bodies comprising petalite, spodumene, lepidolite, biotite, mica, muscovite, feldspar, microcline, beryl, Li-muscovite, lithiophilite, amblygonite, illite, cookeite, albite, analcime, squi, amphiboles and/or other minerals mentioned throughout or any combinations thereof.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defusing a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method to recover cesium, rubidium, or both from secondary ore, wherein said secondary ore comprises 25 wt % $Cs_2O$ or less based on overall weight of said secondary ore and the majority of said secondary ore comprise pieces having at least one dimension that is over 5 inches (12.7 cm), said method comprising:

obtaining crushed ore from said secondary ore and separating into at least three different size fractions, wherein said crushed ore comprising individual pieces, each piece having a size capable of passing through a U.S. standard sieve mesh/screen opening of 3 inches (76.2mm);

conducting an initial calibration step, wherein before said passing of said crushed ore through a sorter, passing through, as size fractions, known rocks and minerals having size fractions that are the same as the at least three different size fractions of separated secondary ore, and that are representative of the rocks and minerals in said secondary ore to be sorted so as to calibrate said sorter, for each size fraction, with respect to what is representative of a "Grade 1 piece" or what is representative of a "Grade 2 piece" or both based on scanned properties of atomic number or material density or both;

setting the sorter to sort for a desired size fraction selected from one of said at least three different size fractions;

passing said desired size fraction of said crushed ore through said a sorter to conduct a sorting at a feed rate of at least 1 ton/hour, wherein said sorter determines whether each individual piece of crushed ore is said "Grade 1 piece" or said "Grade 2 piece", based on said sorter conducting at least one scan of each individual piece and determining atomic number or material density or both of each individual piece, wherein said "Grade 1 piece" comprises $Cs_2O$, or $Cs_2O$ and $Rb_2O$ together, in an amount of at least 20% based on the weight of said individual piece and said "Grade 2 piece" is any of said crushed ore that is not a "Grade 1 piece";

separating said Grade 1 pieces from said Grade 2 pieces, whereby wt % $Cs_2O$ of said Grade 1 pieces is at least 10% by weight higher than wt % $Cs_2O$ in said secondary ore; and wherein said secondary ore comprises pollucite, nanpingite, carnallite, rhodozite, pezzottaite, rubicline, borate ramanite, beryls, voloshonite, cesstibtantite, avogadrite, margaritasite, kupletskite, nalivkinite, petalite, spodumene, lepidolite, biotite, mica, muscovite, feldspar, microcline, Li-muscovite, lithiophilite, amblygonite, illite, cookeite, albite, analcime, squi, amphiboles, lithian mica, amphibolite, lithiophospahe, apatite, londonite, or any combinations thereof.

2. The method of claim 1, further comprising extracting cesium, rubidium or both by subjecting said Grade 1 pieces to at least one acid treatment.

3. The method of claim 1, wherein said secondary ore comprises 20 wt % $Cs_2O$ or less.

4. The method of claim 1, further comprising calcining said Grade 1 pieces after said separating.

5. The method of claim 1, wherein said secondary ore comprises pollucite.

6. The method of claim 1, wherein said sorter detects and selects said Grade 1 piece based on an atomic number of at least 80.

7. The method of claim 1, wherein said sorter detects and selects said Grade 1 piece based on an atomic number of from 80 to 150.

8. The method of claim 1, wherein said method captures at least about 40% by weight of available $Cs_2O$ present in said secondary ore.

9. The method of claim 1, wherein said method captures at least about 10% by weight of available $Rb_2O$ present in said secondary ore.

10. The method of claim 1, further comprising a second sorting step comprising passing said Grade 2 pieces through a second sorter, which is the same or different from said sorter, wherein said second sorter determines whether each individual piece of said Grade 2 pieces is a "Grade 2A piece" or "Grade 2B piece", based on said second sorter conducting at least one scan of each individual piece and determining atomic number or material density or both of each individual piece, wherein said "Grade 2A piece" comprises $Rb_2O$ in an amount of at least 20% based on the weight of said individual piece, and said "Grade 2B piece" is any Grade 2 piece that is not a Grade 2A piece and then separating said Grade 2A pieces from said Grade 2B pieces.

11. The method of claim 10, wherein said second sorter is set such that said Grade 2A piece is determined based on an atomic number of at least 50.

12. The method of claim 10, wherein said second sorter is set such that said Grade 2A piece is determined based on an atomic number of from 60 to 150.

13. The method of claim 10, wherein said second sorting captures at least about 10% by weight of available $Cs_2O$ present in said secondary ore, based on weight of said secondary ore at start.

14. The method of claim 10, wherein said second sorting captures at least about 20% by weight of available $Rb_2O$ present in said secondary ore, based on weight of said secondary ore at start.

15. The method of claim 10, wherein said first sorting and said second sorting combined capture at least 60% by weight of available $Cs_2O$ present in said secondary ore, based on weight of said secondary ore at start.

16. The method of claim 10, wherein said first sorting and said second sorting combined capture at least 80% by weight of available $Cs_2O$ present in said secondary ore, based on weight of said secondary ore at start, and at least 60% by weight of available $Rb_2O$ present in said secondary ore, based on weight of said secondary ore at start.

17. The method of claim 1, wherein said Grade 1 pieces comprise at least 100% more $Cs_2O$ based on a comparison of weight percent of $Cs_2O$ in secondary ore to weight percent of $Cs_2O$ in Grade 1 pieces.

18. The method of claim 1, wherein said Grade 1 pieces comprise at least 300% more $Cs_2O$ based on a comparison of weight percent of $Cs_2O$ in secondary ore to weight percent of $Cs_2O$ in Grade 1 pieces.

19. The method of claim 10, further comprising extracting cesium, rubidium or both by subjecting said Grade 2A pieces to at least one non-acid treatment.

20. The method of claim 1, wherein said secondary ore comprises rhodozite, pezzottaite, borate ramanite, beryls, cesstibtantite, avogadrite, margaritasite, kupletskite, nalivkinite, londonite, or any combinations thereof.

21. The method of claim 1, wherein said secondary ore comprises rubicline, borate ramanite, voloshonite, or any combinations thereof 22. The method of claim 1, wherein said sorter is set such that Grade 1 piece is determined based on a material density of at least 2.5 $g/cm^3$.

23. The method of claim 1, wherein said sorter is set such that Grade 1 piece is determined based on a material density of a range of from 2.5 $g/cm^3$ to 3.5 $g/cm^3$.

24. The method of claim 1, wherein said sorter conducts at least 2 scans of each individual piece, wherein one scan determines atomic number and the other scan determines material density.

25. The method of claim 10, wherein said second sorter is set such that said Grade 2A piece is determined based on material density of at least 2.5 $g/cm^3$.

26. The method of claim 10, wherein second sorter is set such that said Grade 2A is determined based on an atomic number of at least 30 and a material density of at least 2.5 $g/cm^3$.

27. The method of claim 1, wherein said "Grade 1 piece" is determined based on being within 10% of the scanned property of atomic number or material density or both for the representative Grade 1 piece for that size fraction.

28. The method of claim 1, wherein said at least three different size fractions are selected from the following five size fractions (U.S. Standard Sieve Size):
−2 inches +1.5 inches
−1.5 inches +1 inch
−1 inch +0.5 inch
−0.5 inch +0.25 inch
−0.25 inch +0.125 inch.

29. The method of claim 1, wherein said separating the crushed ore comprising individual pieces comprises separating into five size fractions: (a) −2 inches +1.5 inches; (b) −1.5 inches +1 inch; (c) −1 inch +0.5 inch; (d) −0.5 inch +0.25 inch; and (3) −0.25 inch +0.125 inch.

30. The method of claim 1, wherein the at least three size fractions are acquired by the formulas:

$$S_1 = S_x \text{ to } 50\% \, S_x$$

$$S_2 = S_1 \text{ to } 50\% \, S_1$$

$$S_3 = S_2 \text{ to } 50\% \, S_2, \text{ and}$$

optionally $S_4 = S_3$ to 50% $S_3$, where $S_X$ is the maximum size fraction that is capable of passing through the sorter, and $S_1$, $S_2$, $S_3$, and $S_4$ are each a different size fraction.

* * * * *

UNITED STATES PATENT AND TRADEMARK OFFICE
CERTIFICATE OF CORRECTION

Page 1 of 1

PATENT NO. : 9,045,812 B2
APPLICATION NO. : 14/277914
DATED : June 2, 2015
INVENTOR(S) : Bart Bakke et al.

It is certified that error appears in the above-identified patent and that said Letters Patent is hereby corrected as shown below:

IN THE CLAIMS

Column 38, line 1: "piece having" should read -- having --; line 18: "a sorter" should read -- sorter --.

Signed and Sealed this
Sixth Day of October, 2015

Michelle K. Lee
*Director of the United States Patent and Trademark Office*